(12) United States Patent
Wilson et al.

(10) Patent No.: US 8,815,509 B2
(45) Date of Patent: Aug. 26, 2014

(54) FLUORESCENCE-BASED ASSAY FOR THE RAPID DETECTION AND QUANTIFICATION OF DEOXYRIBONUCLEOSIDE TRIPHOSPHATES

(75) Inventors: Peter M. Wilson, Pasadena, CA (US); Robert D. Ladner, Santa Monica, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 13/523,782

(22) Filed: Jun. 14, 2012

(65) Prior Publication Data
US 2013/0029331 A1    Jan. 31, 2013

Related U.S. Application Data

(60) Provisional application No. 61/496,918, filed on Jun. 14, 2011.

(51) Int. Cl.
| | |
|---|---|
| C12Q 1/68 | (2006.01) |
| C12P 19/34 | (2006.01) |
| G01N 21/64 | (2006.01) |
| G01N 21/66 | (2006.01) |
| G01N 31/22 | (2006.01) |
| G01N 33/52 | (2006.01) |
| C07H 21/04 | (2006.01) |
| C07H 21/02 | (2006.01) |
| C07H 19/04 | (2006.01) |

(52) U.S. Cl.
CPC .......... *C12Q 1/6844* (2013.01); *G01N 21/6428* (2013.01)
USPC ....... 435/6.1; 435/6.12; 435/91.2; 422/82.08; 422/430; 536/24.3; 536/24.33; 536/25.32; 536/26.6

(58) Field of Classification Search
CPC .. C12Q 1/6806; C12Q 1/6837; C12Q 1/6869; C12Q 1/6874; G01N 21/6428
USPC .............. 435/6.1, 6.12, 91.2; 422/82.08, 430; 536/24.3, 24.33, 25.32, 26.6
See application file for complete search history.

(56) References Cited

U.S. PATENT DOCUMENTS 5,538,848 A * 7/1996 Livak et al. .................. 435/6.16

OTHER PUBLICATIONS

Wilson et al, A novel fluorescence-based assay for the rapid detection and quantification of cellular deoxyribonucleoside triphosphates, 2011, Nucleic Acids Research, 39, e112, pp. 1-15.*
Roy et al, Simultaneous Determination of Pyrimidine or Purine Deoxyribonucleoside Triphosphates Using a Polymerase Assay, 1999, Analytical Biochemistry 269, 403-409.*
Johansson, Choosing reporter-quencher pairs for efficient quenching through formation of intramolecular dimers, Methods Mol. Biol., 2006, 335, 17-29.*
Johansson, Choosing reporter-quencher pairs for efficient quenching through formation of intramolecular dimers, Methods Mol. Biol., 2006, 335, 17-29, front page (for the support of date), printed on Jul. 13, 2013.*

* cited by examiner

*Primary Examiner* — Narayan Bhat
(74) *Attorney, Agent, or Firm* — Brian T. Duke; Nixon Peabody LLP

(57) ABSTRACT

The inventors have developed a rapid and sensitive fluorescence-based assay to quantify dNTPs. This assay relies on the principle that incorporation of a limiting dNTP is required for primer-extension and polymerase-mediated 5-3' exonuclease hydrolysis of a quenched fluorophore-labeled probe resulting in fluorescence. The concentration of limiting dNTPs is directly proportional to the fluorescence generated. This assay has important applications in research that investigates the influence of pathological conditions or pharmacological agents on dNTP biosynthesis and regulation.

25 Claims, 10 Drawing Sheets

```
                              SEQUENCE LISTING

<160> NUMBER OF SEQ ID NOS: 18

<210> SEQ ID NO 1
    <211> LENGTH: 14
    <212> TYPE: DNA
    <213> ORGANISM: Homo sapiens

<400> SEQUENCE: 1
ccgcctccac cgcc                                                      14

<210> SEQ ID NO 2
    <211> LENGTH: 23
    <212> TYPE: DNA
    <213> ORGANISM: Homo sapiens

<400> SEQUENCE: 2
aggaccgagg caagagcgag cga                                            23

<210> SEQ ID NO 3
    <211> LENGTH: 54
    <212> TYPE: DNA
    <213> ORGANISM: Homo sapiens

<400> SEQUENCE: 3
tcgctcgctc ttgcctcggt ccttattatt attattatta ggcggtggag gcgg          54

<210> SEQ ID NO 4
    <211> LENGTH: 47
    <212> TYPE: DNA
    <213> ORGANISM: Homo sapiens

<400> SEQUENCE: 4
tcgctcgctc ttgcctcggt cctttattta tttggcggtg gaggcgg                  47

<210> SEQ ID NO 5
    <211> LENGTH: 43
    <212> TYPE: DNA
    <213> ORGANISM: Homo sapiens

<400> SEQUENCE: 5
tcgctcgctc ttgcctcggt cctttatttg gcggtggagg cgg                      43

<210> SEQ ID NO 6
    <211> LENGTH: 23
    <212> TYPE: DNA
    <213> ORGANISM: Homo sapiens

<400> SEQUENCE: 6
tggtccgtgg cttgtgcgtg cgt                                            23

<210> SEQ ID NO 7
    <211> LENGTH: 47
    <212> TYPE: DNA
```

<213> ORGANISM: Homo sapiens

<400> SEQUENCE: 7
acgcacgcac aagccacgga ccaaataaat aaaggcggtg gaggcgg     47

<210> SEQ ID NO 8
<211> LENGTH: 43
<212> TYPE: DNA
<213> ORGANISM: Homo sapiens

<400> SEQUENCE: 8
acgcacgcac aagccacgga ccaaataaag gcggtggagg cgg     43

<210> SEQ ID NO 9
<211> LENGTH: 23
<212> TYPE: DNA
<213> ORGANISM: Homo sapiens

<400> SEQUENCE: 9
aggattgagg taagagtgag tgg     23

<210> SEQ ID NO 10
<211> LENGTH: 47
<212> TYPE: DNA
<213> ORGANISM: Homo sapiens

<400> SEQUENCE: 10
ccactcactc ttacctcaat cctttgtttg tttggcggtg gaggcgg     47

<210> SEQ ID NO 11
<211> LENGTH: 43
<212> TYPE: DNA
<213> ORGANISM: Homo sapiens

<400> SEQUENCE: 11
ccactcactc ttacctcaat cctttgtttg gcggtggagg cgg     43

<210> SEQ ID NO 12
<211> LENGTH: 23
<212> TYPE: DNA
<213> ORGANISM: Homo sapiens

<400> SEQUENCE: 12
accattcacc tcacactcac tcc     23

<210> SEQ ID NO 13
<211> LENGTH: 47
<212> TYPE: DNA
<213> ORGANISM: Homo sapiens

<400> SEQUENCE: 13
ggagtgagtg tgaggtgaat ggtttctttc tttggcggtg gaggcgg     47

<210> SEQ ID NO 14
<211> LENGTH: 43
<212> TYPE: DNA
<213> ORGANISM: Homo sapiens

<400> SEQUENCE: 14
ggagtgagtg tgaggtgaat ggtttctttg gcggtggagg cgg     43

<210> SEQ ID NO 15
<211> LENGTH: 16

```
<212> TYPE: DNA
<213> ORGANISM: Homo sapiens

<400> SEQUENCE: 15
attattatta ttatta                                                      16

<210> SEQ ID NO 16
<211> LENGTH: 3
<212> TYPE: DNA
<213> ORGANISM: Homo sapiens

<400> SEQUENCE: 16 taa                                                                     3

<210> SEQ ID NO 17
<211> LENGTH: 10
<212> TYPE: DNA
<213> ORGANISM: Homo sapiens

<400> SEQUENCE: 17
taataataat                                                             10

<210> SEQ ID NO 18
<211> LENGTH: 16
<212> TYPE: DNA
<213> ORGANISM: Homo sapiens

<400> SEQUENCE: 18
taataataat aataat                                                      16
```

FLUORESCENCE-BASED ASSAY FOR THE RAPID DETECTION AND QUANTIFICATION OF DEOXYRIBONUCLEOSIDE TRIPHOSPHATES

CROSS-REFERENCE TO RELATED APPLICATIONS

This application claims priority from U.S. Provisional Patent Application No. 61/496,918, filed on Jun. 14, 2011, which is incorporated herein by reference in its entirety.

STATEMENT REGARDING FEDERALLY SPONSORED RESEARCH

The U.S. Government has a paid-up license in this invention and the right in limited circumstances to require the patent owner to license others on reasonable terms as provided for by the terms of Grant No. CA14089 received from the National Institutes of Health.

FIELD OF INVENTION

This invention generally relates to a fluorescence-based assay for the detection and quantification of deoxyribonucleoside triphosphates.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

The coordinated regulation of intracellular deoxyribonucleoside triphosphate (dNTP) pools is important for the fidelity of DNA synthesis during DNA replication and repair in both prokaryotic and eukaryotic organisms. Dysregulation of intracellular dNTP pools is observed in a large number of pathological conditions and represents a critical mechanism of action of a number of pharmacological inhibitors. The quantification of cellular dNTP levels is therefore of fundamental importance in understanding the mechanisms of action of pharmacological agents and the biology of physiological and pathological phenomena that result in altered dNTP biosynthesis. Thus, there is a need in the art for a rapid, sensitive and reproducible fluorescence-based method for measuring dNTPs.

SUMMARY OF THE INVENTION

In some embodiments, the invention teaches a method for quantifying deoxyribonucleoside triphosphates (dNTPs), including: providing an oligonucleotide template, including a primer binding region, a dNTP detection region and a fluorophore-labeled probe binding region; hybridizing a fluorophore-labeled probe to the fluorophore-labeled probe binding region and hybridizing a primer to the primer binding region, whereby a TPP complex is formed, and wherein the fluorophore-labeled probe includes a fluorophore and one or more quenching molecules; providing a polymerase; combining the TPP complex to which the polymerase is bound with a sample including one or more dNTPs; exciting the fluorophore; detecting a resulting fluorescence; and quantifying the dNTPs in the sample, based upon the resulting fluorescence. In some embodiments, one or more of the quenching molecules is a non-emissive (dark) quenching molecule selected from the group consisting of: ZEN, IBFQ, BHQ-1, BHQ-2, DDQ-I, DDQ-II, Dabcyl, Qxl quencher, Iowa Black RQ, and IRDye QC-1. In some embodiments, the sample including one or more dNTPs includes an intracellular sample of dNTPs. In some embodiments, the intracellular sample is derived from one or more cancer cells. In some embodiments, the intracellular sample is derived from one or more cells that have been exposed to one or more chemotherapeutic agents. In certain embodiments, the polymerase includes Taq polymerase. In certain embodiments, the fluorophore is selected from the group consisting of: 6-FAM, TET, HEX, Cy3, TMR, ROX, Texas Red, Cy5, LC red 705 and LC red 640. In certain embodiments, the oligonucleotide template includes one or more quenchers. In certain embodiments, one or more of the quenchers is a non-fluorescent quencher selected from the group consisting of BHQ-1 and BHQ-2. In certain embodiments, one or more of the quenchers is located on a region of the oligonucleotide template within 1-5 bases of the base opposite where a 5' end of the fluorophore-labeled probe would hybridize under hybridizing conditions.

In various embodiments, the invention teaches a kit for detecting deoxyribonucleoside triphosphates (dNTPs), including an oligonucleotide template, wherein the oligonucleotide template includes a primer binding region, a dNTP detection region and a fluorophore-labeled probe binding region. In some embodiments, the kit further includes a fluorophore-labeled probe, wherein the fluorophore-labeled probe is complementary to the fluorophore-labeled probe binding region of the oligonucleotide template, and wherein the fluorophore-labeled probe includes a fluorophore and one or more quenching molecules. In some embodiments, one or more of the quenching molecules is a non-emissive (dark) quenching molecule selected from the group consisting of: ZEN, IBFQ, BHQ-1, BHQ-2, DDQ-I, DDQ-II, Dabcyl, Qxl quencher, Iowa Black RQ, and IRDye QC-1. In some embodiments, the kit further includes a primer. In some embodiments, the kit further includes a quantity of dNTPs. In some embodiments, the kit further includes a polymerase. In certain embodiments, the polymerase is Taq polymerase. In certain embodiments, the kit includes instructions for detecting one or more dNTPs. In some embodiments, the kit includes a means for collecting intracellular dNTPs. In some embodiments, the means for collecting intracellular dNTPs is configured to collect intracellular dNTPs from a eukaryotic cell. In some embodiments, the eukaryotic cell is a cancer cell. In some embodiments, the fluorophore is selected from the group consisting of: 6-FAM, TET, HEX, Cy3, TMR, ROX, Texas Red, Cy5, LC red 705 and LC red 640. In some embodiments, the oligonucleotide template includes one or more quenchers. In some embodiments, one or more of the quenchers is a non-fluorescent quencher selected from the group consisting of BHQ-1-dT and BHQ-2. In some embodiments, one or more of the quenchers are located on a region of the oligonucleotide template within 1-5 bases of the base opposite where a 5' end of the fluorophore-labeled probe would hybridize under hybridizing conditions.

In various embodiments, the invention teaches a composition including an oligonucleotide template, wherein the oligonucleotide template includes a primer binding region, a dNTP detection region and a fluorophore-labeled probe binding region; a fluorophore-labeled probe bound to said oligonucleotide template, wherein the fluorophore-labeled probe includes a fluorophore and one or more quenching molecules;

and a primer bound to said oligonucleotide template. In some embodiments, one or more of the quenching molecules is a non-emissive (dark) quenching molecule selected from the group consisting of: ZEN, IBFQ, BHQ-1, BHQ-2, DDQ-I, DDQ-II, Dabcyl, Qxl quencher, Iowa Black RQ, and IRDye QC-1. In some embodiments, the oligonucleotide template further includes one or more quenchers. In some embodiments, one or more of the quenchers are located on a region of the oligonucleotide template within 1-5 bases of the base opposite where a 5' end of the fluorophore-labeled probe would hybridize under hybridizing conditions.

BRIEF DESCRIPTION OF THE DRAWINGS

Exemplary embodiments are illustrated in the referenced figures. It is intended that the embodiments and figures disclosed herein are to be considered illustrative rather than restrictive.

DESCRIPTION OF THE INVENTION

Figure 1:
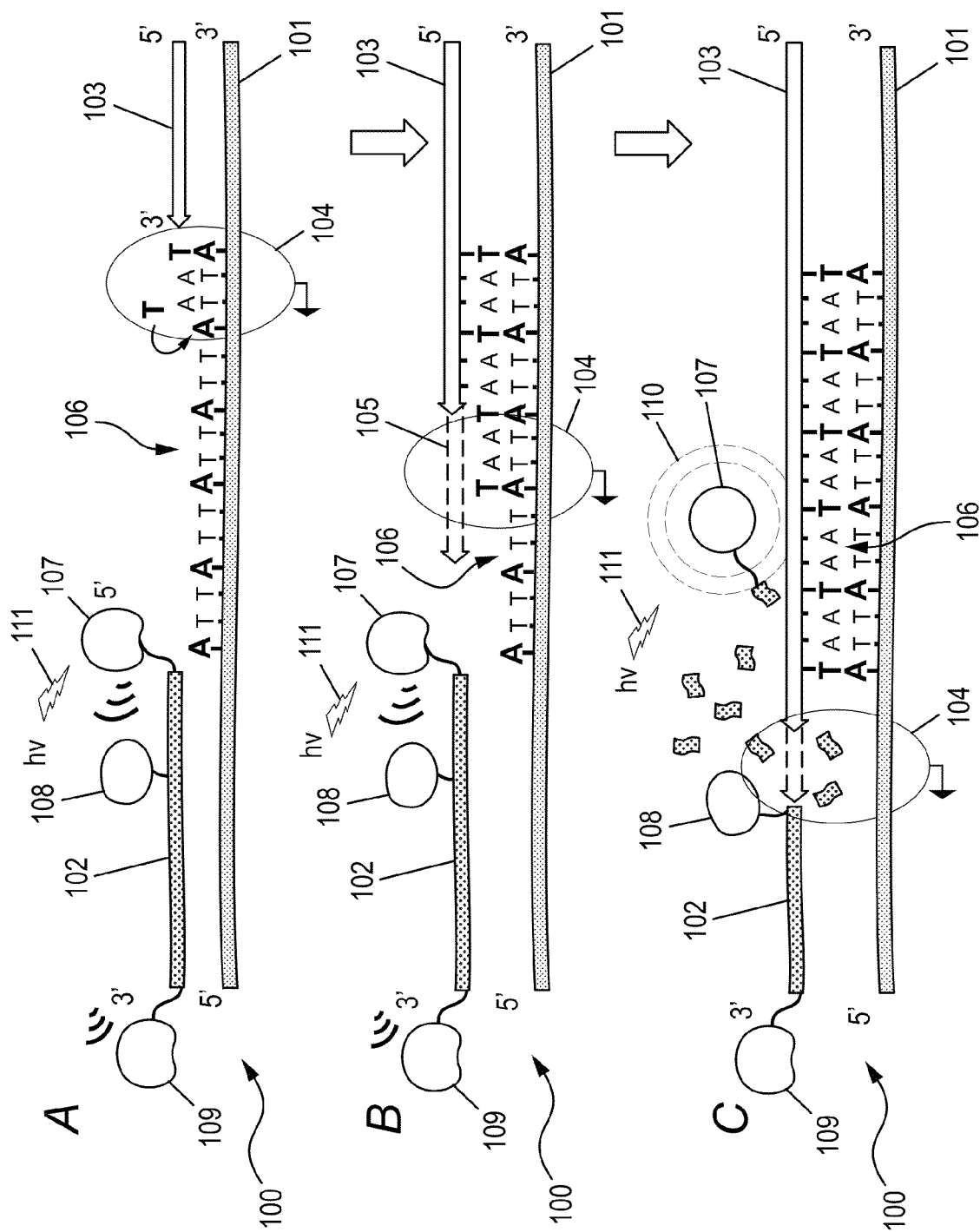
FIG. 1 demonstrates, in accordance with an embodiment of the invention, a simplified schematic illustrating the principal mechanism involved in the fluorescence-based assay for measuring dNTP concentrations. Detection of dTTP using a template 101 (which includes the sequence of SEQ ID NO: 15 in this particular non-limiting embodiment) is given as the example. The template 101, probe 102 and primer 103 are labeled in the drawing. Briefly, as the temperature declines from the 95° C. hot-start, the probe 102 anneals to the template 101 first (65-70° C.), followed by the primer 103 at 60° C. to form the TPP complex 100, at which point the polymerase 104 begins extension of the nascent strand 105. In the presence of a sufficient concentration of limiting dNTP (6 dTTP molecules in the example shown), successful primer extension occurs (as demonstrated by the progressively longer nascent strand, which includes SEQ ID NO: 16, 17 and 18 in part A, B and C of the figure respectively, in this particular non-limiting embodiment) through the mid-template dNTP detection region 106 and the polymerase 104 cleaves the terminal nucleotide labeled with a fluorophore 107 via its 5'-3' exonuclease activity, releasing it from the dual-quenched 108 and 109 probe 102, resulting in disruption of FRET and generation of a fluorescence signal 110 in response to excitation-induced photon energy (hv) 111. When the dNTP being measured (dTTP) is not present, or becomes exhausted, the polymerase 104 stalls, extension is inhibited/terminated, fluorescence remains quenched via FRET and the probe 102 remains dark. In any given reaction, the level of fluorescence generated is directly proportional to the concentration of the limiting dNTP. The dAMP molecules enlarged in the template strand represent the nucleotides opposite which the limiting dTTP nucleotides (also enlarged and in bold) will base pair. Only the nucleotide sequence found in the mid-template dNTP detection region 106 is given for simplicity. The complete sequences of all templates (including primer- and probe-binding regions), primer NDP1 and detection probes used in the specific experiments described herein are given in Table 1.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3rd ed., J. Wiley & Sons (New York, N.Y. 2001); March, *Advanced Organic Chemistry Reactions, Mechanisms and Structure* 5th ed., J. Wiley & Sons (New York, N.Y. 2001); and Sambrook and Russell, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"dNTP" as used herein is an acronym for deoxyribonucleoside triphosphate.

"NFU" as used herein is an acronym for normalized fluorescence units.

"DT" as used herein is an acronym for detection template.

"NDP1" as used herein is an acronym for nucleotide detection primer 1.

"IBFQ" as used herein is an acronym for Iowa black fluorescein quencher.

"6-FAM" as used herein is an acronym for 5'-carboxyfluorescein.

"HPLC" as used herein is an acronym for high-performance liquid chromatography.

"LC-MS/MS" as used herein is an acronym for liquid chromatography mass spectrometry.

"LOQ" as used herein is an acronym for limit of quantification.

"LOD" as used herein is an acronym for limit of detection.

"PBS" as used herein is an acronym for phosphate buffered saline.

"rNTP" as used herein is an acronym for ribonucleoside triphosphate.

"TPP complex" as used herein is an abbreviation of template:primer:probe complex.

"FRET" as used herein is an acronym for Förster resonance energy transfer.

"TS" as used herein is an acronym for thymidylate synthase.

"FUdR" as used herein is an acronym for fluorodeoxyuridine.

"dUTP" as used herein is an acronym for deoxyuridine triphosphate.

"DUT" as used herein is an acronym for dUTPase.

"Conditions" and "disease conditions" as used herein may include, but are in no way limited to cancer, conditions associated therewith or combinations thereof.

"Mammal" as used herein, refers to any member of the class Mammalia, including without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

In some embodiments, the numbers expressing quantities of ingredients, properties such as molecular weight, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

In the present invention, the inventors disclose a rapid and sensitive fluorescence-based assay with throughput capability to detect and measure dNTPs as an alternative to currently employed approaches that utilize radioisotope-based DNA polymerase assays or HPLC and/or LC-MS/MS methodology. The inventors developed a DNA polymerase-based approach utilizing a modified oligonucleotide template with 3 distinct regions: a 3' primer binding region, a mid-template dNTP detection region and a 5' 6-FAM-labeled probe binding region. During the reaction, the probe and primer hybridize to the oligonucleotide template to form the template:primer:probe complex (TPP complex). When Taq polymerase binds to the primer in the TPP complex and the dNTP to be measured is present, successful extension of the nascent strand occurs and the inherent 5' to 3' exonuclease activity of Taq polymerase cleaves and displaces the 6-FAM-labeled probe in a 5' to 3' direction, releasing the 6-FAM fluorophore from its proximity to the two quenchers. This displacement effectively disrupts the Förster resonance energy transfer (FRET) and the resulting fluorescence detected upon excitation is directly proportional to the amount of the limiting dNTP available in the assay for incorporation (FIG. 1). Conversely, when the limiting dNTP becomes exhausted and is no longer available for incorporation, Taq polymerase stalls and extension delay and/or chain termination of the nascent strand occurs. In this instance, probe hydrolysis/degradation does not occur and the probe remains dark as fluorescence remains quenched via FRET.

In some embodiments, the invention teaches a method for quantifying deoxyribonucleoside triphosphates (dNTPs), including: providing an oligonucleotide template, including a primer binding region, a limiting dNTP detection region and a fluorophore-labeled probe binding region; hybridizing a fluorophore-labeled probe to the fluorophore-labeled probe binding region and hybridizing a primer to the primer binding region, whereby a TPP complex is formed, and wherein the fluorophore-labeled probe includes a fluorophore and one or more quenching molecules; providing a polymerase; combining the TPP complex to which the polymerase is bound with a sample containing one or more dNTPs; exciting the fluorophore; detecting a resulting fluorescence; and quantifying the dNTPs in the sample, based upon the resulting fluorescence. In some embodiments, one or more of the quenching molecules is a non-emissive (dark) quenching molecule selected from the group consisting of: ZEN, Eclipse, BHQ-1, BHQ-2, DDQ-I, DDQ-II, Dabcyl, Qxl quencher, Iowa Black FQ, Iowa Black RQ, and IRDye QC-1. One of skill in the art would readily appreciate that any dark quencher compatible with the fluorophore with an absorption maximum of 430-670 nm could be used. In an embodiment of the invention, the fluorophore-labeled probe includes ZEN and IBFQ. One of skill in the art would appreciate that any compatible quencher and fluorophore pairing could be implemented within the inventive method to accomplish a substantially similar overall effect. The quencher need not be a dark quencher, so long as it is compatible with the fluorophore used. In some embodiments, the sample containing dNTPs includes intracellular dNTPs. In certain embodiments, the intracellular dNTPs are obtained from one or more prokaryotic cells. In certain embodiments, the intracellular dNTPs are obtained from one or more eukaryotic cells. In certain embodiments, the intracellular dNTPs are obtained from one or more mammalian cells. In certain embodiments, the intracellular dNTPs are obtained from one or more cancer cells. In some embodiments, the intracellular dNTPs are obtained from one or more cells that have been exposed to one or more pharmacalogical agents. In certain embodiments, the intracellular dNTPs are obtained from one or more cells that have been exposed to one or more chemotherapeutic agents. Merely by way of example, one or more of the chemotherapeutic agents can include, but are in no way limited to fluorodeoxyuridine (FUdR), 5-fluorouracil (5-FU), pemetrexed, raltitrexed, and ZD9331. One of skill in the art would readily appreciate the chemotherapeutic agent could be any small molecule inhibitor of thymidylate synthase (TS).

In some preferred embodiments, the polymerase used in the inventive method is Taq polymerase. One of skill in the art would readily appreciate that one or more alternative polymerases with similar characteristics, including 5' to 3' exonuclease activity, could be used in the inventive method.

In certain embodiments, one or more fluorophores incorporated into the fluorescent probe used with the inventive method are selected from the group consisting of: 6-FAM, TET, HEX, Cy3, TMR, ROX, Texas Red, Cy5, LC red 705 and LC red 640. One of skill in the art would readily appreciate that numerous additional fluorophores with similar characteristics could be used in addition to or as an alternative to those described herein.

In some embodiments, the oligonucleotide template used in conjunction with the inventive method includes one or more quenchers. In some embodiments, one or more of the quenchers is a non-fluorescent quencher selected from the group consisting of BHQ-1 and BHQ-2. One of skill in the art would readily appreciate that any quenching molecule that is compatible with the corresponding probe fluorophore and supports replicative template function could also be used within the inventive method. In various embodiments, one or more of the quenchers is positioned on a region of the oligonucleotide template within 1-5 bases of the base opposite where a 5' end of the fluorophore-labeled probe would hybridize under hybridizing conditions.

In various embodiments, the oligonucleotide templates used in conjunction with the inventive method may have a range of sensitivities and linear capabilities for any particular dNTP. In some embodiments, the oligonucleotide template used with the inventive method requires the incorporation of one limiting dNTP per TPP complex to yield fluorescence. In other embodiments, the oligonucleotide template requires the incorporation of two limiting dNTPs per TPP complex to yield fluorescence. In other embodiments, the oligonucleotide template requires the incorporation of three limiting dNTPs per TPP complex to yield fluorescence. In other embodiments, the oligonucleotide template requires the incorporation of four limiting dNTPs per TPP complex to yield fluorescence. In other embodiments, the oligonucleotide template requires the incorporation of five limiting dNTPs per TPP complex to yield fluorescence. In other embodiments, the oligonucleotide template requires the incorporation of six limiting dNTPs per TPP complex to yield fluorescence. In other embodiments, the oligonucleotide template requires the incorporation of seven limiting dNTPs per TPP complex to yield fluorescence. In other embodiments, the oligonucleotide template requires the incorporation of eight or more limiting dNTPs per TPP complex to yield fluorescence.

In various embodiments, the invention teaches a kit for detecting deoxyribonucleoside triphosphates (dNTPs), including an oligonucleotide template, wherein the oligonucleotide template includes a primer binding region, a dNTP detection region and a fluorophore-labeled probe binding region. In certain embodiments, the kit includes a fluorophore-labeled probe, wherein the fluorophore-labeled probe is complementary to the fluorophore-labeled probe binding region of the oligonucleotide template, and wherein the fluorophore-labeled probe includes a fluorophore and one or more quenching molecules. In some embodiments, one or more of the quenching molecules is a non-emissive (dark) quenching molecule selected from the group consisting of: ZEN, Eclipse, BHQ-1, BHQ-2, DDQ-I, DDQ-II, Dabcyl, Qxl quencher, Iowa Black FQ, Iowa Black RQ, and IRDye QC-1. One of skill in the art would readily appreciate that any dark quencher compatible with the fluorophore with an absorption max of 430-670 nm could be included in the inventive kit. One of skill in the art would also appreciate that any compatible quencher and fluorophore pairing could be alternatively included in the inventive kit to accomplish a substantially similar overall effect. The quencher need not be a dark quencher, so long as it is compatible with the fluorophore used.

In certain embodiments, one or more fluorophores included in the fluorophore-labeled probe of the inventive kit is selected from the group consisting of: 6-FAM, TET, HEX, Cy3, TMR, ROX, Texas Red, Cy5, LC red 705 and LC red 640. One of skill in the art would readily appreciate that numerous additional fluorophores with similar characteristics could be included in addition or as an alternative to those described herein.

In some embodiments, the oligonucleotide template included in the kit includes one or more quenchers. In certain embodiments, one or more of the quenchers is a non-fluorescent quencher selected from the group consisting of BHQ-1 and BHQ-2. One of skill in the art would readily appreciate that any quenching molecule that is compatible with the corresponding probe fluorophore and supports replicative template function could be included in the inventive kit alternatively or in addition to those quenchers specifically described herein. In various embodiments, one or more of the quenchers are located on a region of the oligonucleotide template within 1-5 bases of the base opposite where a 5' end of the fluorophore-labeled probe would hybridize under hybridizing conditions.

In some embodiments, the kit includes an oligonucleotide template described herein, but does not include a fluorophore-labeled probe described herein. Alternatively, the kit may include a fluorophore-labeled probe described herein, but not an oligonucleotide template described herein. In some embodiments, the inventive kit includes a primer that is complimentary to a region of the oligonucleotide template. In some embodiments, the kit includes a quantity of one or more types of dNTPs selected from the group consisting of dATPs, dGTPs, dCTPs, dTTPs, dUTPs and combinations thereof. In some embodiments, the kit includes a polymerase. In some preferred embodiments, the polymerase included in the kit is Taq polymerase. One of skill in the art would readily appreciate that alternative polymerases with similar characteristics to Taq polymerase, including 5' to 3' exonuclease activity, could be additionally or alternatively included in the kit.

In certain embodiments, the kit includes a means for collecting intracellular dNTPs. In certain embodiments, the means for collecting intracellular dNTPs includes materials and reagents used to collect dNTPs from a eukaryotic cell according to one or more methods described in the "Examples" section herein. One of skill in the art would readily appreciate that alternative materials and reagents could be included in the inventive kit in order to facilitate alternative methods known in the art for collecting intracellular samples of dNTPs. Optionally, the kit also contains other components, such as, diluents, buffers, pipetting or measuring tools, or other useful materials as will be readily recognized by those of skill in the art.

The materials and/or components assembled in the kit can be stored and provided in any convenient and suitable ways that preserve their operability and utility. For example one of skill in the art would recognize that certain materials can be dissolved, suspended or dehydrated; they can be provided at room, refrigerated or frozen temperatures. The components are typically contained in suitable packaging material(s). As employed herein, the phrase "packaging material" refers to one or more physical structures used to house the contents of the kit, such as the primers, probes, oligonucleotide templates, dNTPs, chemicals, reagents, materials, measuring instruments and the like. The packaging material is constructed by well-known methods, preferably to provide a sterile, contaminant-free environment. The packaging materials employed in the kit are those customarily utilized in packaging the various individual contents of the inventive kit. As used herein, the term "package" refers to a suitable solid matrix or material such as glass, plastic, paper, foil, and the like, capable of holding the individual kit components. Thus, for example, a package can be a glass or plastic vial used to contain suitable quantities of one or more components of the inventive kit.

The packaging material generally has an external label which indicates the contents and/or purpose of the kit and/or its components. Additionally, instructions for use may be included in the kit. "Instructions for use" typically include a tangible expression describing the technique to be employed in using the components of the kit to affect a desired outcome, such as quantification of dNTPs in a sample.

In certain embodiments, the invention teaches a composition, including: an oligonucleotide template, wherein the oligonucleotide template includes a primer binding region, a dNTP detection region and a fluorophore-labeled probe binding region; a fluorophore-labeled probe bound to said oligonucleotide template, wherein the fluorophore-labeled probe includes a fluorophore and one or more quenching molecules; and a primer bound to said oligonucleotide template. In some embodiments, one or more of the quenching molecules is a non-emissive (dark) quenching molecule selected from the group consisting of: ZEN, Eclipse, IBFQ, BHQ-1, BHQ-2, DDQ-I, DDQ-II, Dabcyl, Qxl quenchers, Iowa Black RQ, and IRDye QC-1. One of skill in the art would readily appreciate that any dark quencher compatible with the fluorophore with an absorption max of 430-670 nm could be incorporated in the inventive composition. One of skill in the art would also appreciate that any compatible quencher and fluorophore pairing could be alternatively included in the inventive composition to accomplish a substantially similar overall effect. The quencher need not be a dark quencher, so long as it is compatible with the fluorophore used. In some embodiments, the oligonucleotide template further includes one or more quenchers. In some embodiments, the one or more quenchers are located on a region of the oligonucleotide template within 1-5 bases of the base opposite where a 5' end of the fluorophore-labeled probe would hybridize under hybridizing conditions.

One skilled in the art will recognize many methods and materials similar or equivalent to those described herein, which could be used in the practice of the present invention. Indeed, the present invention is in no way limited to the methods and materials described.

The following examples are for illustrative purposes only and are not intended to limit the scope of the disclosure or its various embodiments in any way.

EXAMPLES

Example 1

Chemicals, Drugs and Reagents

The oligonucleotide primer, templates and fluorophore- and quencher-labeled detection probes were synthesized by Integrated DNA Technologies (Coralville, Iowa), subjected to polyacrylamide gel electrophoresis purification and reconstituted in Omnipur sterile nuclease-free water (EMD Chemicals USA, Gibbstown N.J.) at a stock concentration of 100 mmol/L. The two non-emissive (dark) quenching molecules incorporated into the detection probes include the Iowa black fluorescein quencher (IBFQ; absorption max 531 nm) and ZEN (non-abbreviation; absorption max 532 nm). The fluorescent label utilized was 6-FAM (5'-carboxyfluorescein; excitation max.=494 nm, emission max.=520 nm). Probes were further diluted to a working stock of 10 µmol/L and aliquoted to avoid repeated freeze/thaw cycles. AmpliTaq Gold DNA Polymerase, GeneAmp 10×PCR Buffer 2, $MgCl_2$ and MicroAmp Optical 96-well Reaction Plates were purchased from Applied Biosystems (Carlsbad, Calif.) and were sealed with ThermalSeal RT2RR sealing film from Excel Scientific (Victorville, Calif.). dNTPs were purchased individually at stock concentrations of 100 mmol/L from New England Biolabs at HPLC-certified >99% purity (Ipswich, Mass.). Ribonucleoside triphosphates (rNTPs) were purchased individually from Applied Biosystems at stock concentrations of 10 mmol/L. Fluorodeoxyuridine (FUdR) and 5-fluorouracil (5-FU) were obtained from Sigma (St Louis, Mo.) and maintained in sterile double-distilled water and DMSO respectively at stock concentrations of 50 mmol/L. Pemetrexed disodium salt (>99%) was purchased from LC Laboratories (Woburn, Mass.) and maintained in sterile double-distilled water at a stock concentration of 50 mmol/L. Recombinant human deoxyuridine nucleotidohydrolase (dUTPase) was expressed and purified as described previously (Ladner et al., *J Biol Chem,* 271, 7745-7751).

Example 2

Assay Components, Instrumentation and Real-Time Fluorescence Conditions

Reaction mixtures contained primer, probe and template at an equimolar final concentration of 0.4 mmol/L. $MgCl_2$ was included at a final concentration of 2 mmol/L. Non-limiting dNTPs were included in the reaction mix in excess at a final concentration of 100 mmol/L (the dNTP to be assayed was excluded). AmpliTaq Gold DNA polymerase was added at 0.875 U/reaction, 2.5 µl of 10×PCR buffer 2 added and nuclease-free $ddH_2O$ added to a final reaction volume of 25 µl. For analysis of cell extracts, the volume of $ddH_2O$ was modified to accommodate the addition of 2.5 µl of cell extract. For dUTP determination from cell extracts, the volume of $ddH_2O$ was further modified to accommodate an additional 1 µl of dUTPase (10 ng/µl). Thermal profiling and fluorescence detection was performed using the 'isothermal' program on board an Applied Biosystems 7500 Real-Time PCR System. For analysis of dNTPs, the thermal profile consisted of a 10 min 95° C. step to 'hot-start' the Taq polymerase and a primer extension time of up to 30 min at 60° C. depending on the application. Raw fluorescence spectra for 6-FAM was measured using filter A at specified time intervals (typically every 5 min) to follow assay progression using Sequence Detection Software (SDS Version 1.4, Applied Biosystems) and exported and analyzed in Microsoft Excel (Microsoft, Redmond Wash.) and Prism (GraphPad Software, La Jolla Calif.). In all cases, fluorescence values for blank reactions (limiting dNTP omitted) were subtracted to give normalized fluorescence units (NFU) to account for background probe fluorescence.

Example 3

Cell Lines and Cell Culture Conditions

The human colorectal cancer cell line HCT116 was purchased from American Type Culture Collection (Lockville, Md.). HCT116 cells were maintained in McCoy's 5A media (Invitrogen) supplemented with 10% fetal bovine serum (Lonza, Walkersville, Md.) with penicillin/streptomycin, sodium pyruvate and L-glutamine (Invitrogen, Carlsbad, Calif.). For pemetrexed analyses, cells were incubated in folate-depleted RPMI supplemented with 25 nmol/L 5-Formyltetrahydrofolate, 10% fetal bovine serum (Lonza), penicillin/streptomycin, sodium pyruvate and L-glutamine for 24 h prior to treatment. Cells were maintained in a humidified Form a incubator (Form a, Waltham, Mass.) at 37° C. with 5% $CO_2$ and routinely screened for mycoplasma using the MycoALERT detection kit (Lonza) and verified mycoplasma negative.

Example 4

Assay Validation, Data Analysis and Statistics

The dNTP detection assay described herein was rigorously tested in accordance with the US Food and Drug Administration 'Analytical Procedures and Methods Validation' and 'Bioanalytical Method Validation' guidelines. The relationship between assay response and known concentrations of the analytes (dNTPs) was analyzed by a 5-point (minimum) calibration curve. Calibration curves were obtained by assaying serial dilutions of dNTP standards diluted with ultra-pure nuclease-free water to the desired concentration and evaluated using regression coefficients ($R^2$). Samples were assayed in triplicate, and experiments were repeated on three independent occasions as appropriate. The limit of detection (LOD) was defined as the mean value of the negative blind controls plus 3 standard deviations (SD) of the mean, i.e. the concentration with a signal to noise ratio of 3:1. The limit of quantification (LOQ) was defined as the mean value of the negative controls plus 5 SD determined from three independent assays (signal to noise ratio of 5:1). Coefficient of variation (% CV) values were calculated from the cumulative mean and SD of replicates. Inter-assay % CVs were calculated from 3 independent experiments performed on different days. The intra-assay % CV represents the mean±SD % CV obtained from assaying replicate samples within 3 identical yet independent assays performed on the same day. The accuracy was assessed by comparing the nominal dNTP concentrations with the corresponding calculated values based on the calibration curve and presented as a percentage. Recoveries were determined by obtaining the result from a known quantity of a dNTP standard spiked into a unknown extract and comparing this to the sum of the individual results obtained for the dNTP standard and the cell extract. All dNTP quantities are expressed as pmoles or pmoles per $10^6$ cells as appropriate.

Example 5

Extraction of Intracellular dNTPs

Cells were plated in 10 cm tissue culture dishes (TPP, Trasadingen, Switzerland) at $1 \times 10^6$ and allowed to adhere and enter log-phase growth for 48 h. Cells were then treated with vehicle or FUdR (1 µmol/L) for 4 h after which the medium was aspirated and cells were rinsed with phosphate-buffered saline (PBS) to remove residual media. The adherent cells were detached by trypsin, resuspended gently in 10 ml of ice-cold PBS and a 100 µA aliquot removed to determine cell number via haemocytometer. The samples were centrifuged for 5 min at 3000 g at 4° C., the supernatant discarded and cell pellets were then resuspended in 500 µl of ice-cold 60% methanol, vortexed vigorously to resuspend, placed at 95° C. for 3 mins and sonicated for 30 s in a Branson Sonifier 450 (Branson, Danbury, Conn.). The extracts were centrifuged (16,000 g for 5 min at 4° C.) to remove cell debris, precipitated protein and DNA. The resultant cell extract supernatants were passed through pre-equilibrated Amicon Ultra-0.5 mL centrifugal filters at 4° C. to remove macromolecules >3 kDa according to the manufacturer's directions (Millipore, Billerica, Mass.). The filtrate was evaporated under centrifugal vacuum at 70° C. and the resultant pellet was resuspended in 25 µl nuclease-free water ready to assay or stored at -80° C. until use.

Example 6

Liquid Chromatography Mass Spectrometry

A previously validated LC-MS/MS approach was utilized to determine dNTP concentrations (Goicoechea et al., *AIDS,* 24, 707-716). Standard solutions of dATP, dTTP, dCTP and dGTP at a concentration of 100 µmol/L were utilized to construct a 9-point calibration curve consisting of 0, 50, 75, 100, 250, 500, 750, 1000 and 2500 ng/mL standards. Each standard was spiked with 100 µl of a mixture of 500 ng/mL dideoxyCTP (ddCTP), 1000 ng/mL of dideoxyGTP (ddGTP), 500 ng/mL of 2-chloroadenosine triphosphate (2-ClA) and 500 ng/mL of ADV-DP to serve as internal quality control standards. Calibration standards were processed simultaneously. Least-square linear regression using a weighting of $1/x^2$ was performed to establish a linear calibration curve between the area ratios of analyte to internal standard and the concentrations of analyte. The linearity was established by the back calculated concentration for each calibration standard. The comparison of the actual concentration to the expected theoretical value established the precision and accuracy of the assay. Samples were vacuum dried using an SPD SpeedVac and suspended in 0.5 mL of 0.01% formic acid in HPLC $H_2O$ which contained 2 units of acid phosphatase/mL (Sigma) and incubated for 30 mins at 37° C., to dephosphorylate and yield the corresponding deoxynucleoside. The dephosphorylated standards and quality controls were vacuum dried in a SPD SpeedVac and reconstituted with 50 µL of 7% methanol in deionized water and 30 µL of the sample was injected into an Agilent 1100 (Agilent, San Jose, Calif.) high performance liquid chromatography (HPLC) system running an ACE C18 column 2.0×50 mm with 3 µm packing (Advanced Chromatography Technologies; Aberdeen, Scotland), coupled to an Sciex API 3000 triple quadrupole tandem mass spectrometer (Applied Biosystems). The operating software was Analyst 1.4.2. A step gradient program was applied to separate all the analytes with a flow rate of 300 µL/min. The mobile phase consisted of methanol as component A and 20 mmol/L ammonia acetate buffer at pH 4.5 as component B. After separation, the analytes in the HPLC efferent were introduced into the mass spectrometer through a Turbolonspray interface coupled with a heated turbo nitrogen stream to evaporate solvents and to increase ionization efficiency. The mass spectrometer operated in distinct periods: The first period had 8 minute scan time for the detection of deoxycytidine (dC), dideoxycytidine (ddC), deoxyguanosine (dG), and dT; the second period lasted 9 min and scanned for deoxyadenosine (dA), dideoxyguanosine (ddG), and 2-ClA. The following mass transitions were monitored—dA: 252→136, retention time of 7 min; dT: 243→127, retention time of 4 min; dG: 268→152, retention time of 3.5 min; dC: 228→112, retention time of 1.5 min; ddC: 212→112, retention time of 3 min; ddG: 252→152, retention time of 7.5 min; ADV: 274→162, retention time of 2 min; 2-ClA: 302→170, retention time of 11 min.

Example 7

Assay Development and Design Considerations

The current assay utilizes an enclosed system wherein the generated fluorescence signal is detected in the presence of any remaining intact fluorophore-labeled probe which, even in its intact and quenched state, will demonstrate some residual background fluorescence. The inventors therefore created a detection system that remains as dark as possible in the absence of analyte-generated signal and thus maintains a high signal to noise ratio that facilitates the detection of low pmole quantities of dNTP required for many applications.

Example 8

Probe Design

A 23 bp oligonucleotide hybridization probe was designed that incorporates two similar napthyl-azo structure-based quenching molecules to maximize the signal to noise ratio. The IBFQ quencher was incorporated at the 3' end of the probe and an additional phosphoramidite internal ZEN quencher was incorporated 9 by from the 5' 6-FAM fluorophore (Table 1). Dark quenchers that have maximum absorption wavelengths in the 531-534 nm range such as IBFQ and ZEN and other functionally-similar and commercially available dark quenchers including black hole quencher 1 (BHQ-1, Sigma; absorption max: 534 nm) and Eclipse (Glen Research, Sterling Va.; absorption max: 530 nm) have demonstrated efficient FRET when coupled with fluorescent dyes that emit in the green to pink spectral range including the 6-FAM fluorophore. The incorporation of two quenching molecules serves two purposes; two quenchers will ensure increased FRET to both quenchers minimizing the quantum yield and background fluorescence generated in the absence of Taq-mediated probe hydrolysis. In addition, the close proximity of the internal ZEN quencher reduces the physical distance between the reporter fluorophore and the quencher to only 9 bp which is an important determinant that increases the efficiency of the FRET mechanism. In addition, while not wishing to be bound by any one particular theory, quenching in linear probes incorporating dark quenchers and fluorescein-based probes such as FAM also occurs via the non-FRET-based mechanism of static quenching, which may further limit assay background and improve signal to noise ratio.

Example 9 dNTP Template and Primer Design

The first oligonucleotide detection template (DT) designed and evaluated for the detection of dTTP was dTTP-DT6 depicted in FIG. 1. This template requires 6 dTTP nucleotides to be available for incorporation into the nascent strand as dTMP (each dTMP event is separated by 2 dAMP incorporation events) by Taq polymerase before the exonuclease activity of Taq cleaves the 6-FAM fluorophore resulting in fluorescence. The requirement for 6 near-sequential dTTP incorporations in the nascent strand greatly limits the probability of fluorescence generated as a result of dNTP miscorporation by Taq polymerase which reportedly can occur in the presence of severely imbalanced dNTP concentrations. However, the requirement for 6 dTTP molecules per probe degradation-induced fluorescence event also has the potential to limit the sensitivity of the assay. To evaluate this, 2 additional oligonucleotide DTs were designed to test the sensitivity capabilities, one requiring 2 dTTPs for incorporation (dTTP-DT2) and a template requiring only a single dTTP for incorporation during primer extension to facilitate probe hydrolysis (dTTP-DT1). The primer utilized (Nucleotide Detection Primer 1; NDP1) was designed complementary to the template 3' region and incorporated a GC clamp. NDP1 was also designed to have a Tm of 56° C. which is 5-10° C. lower than the Tm of the probes at 63-70° C. This facilitates the specific binding order of the probe to the template, followed by the primer to form a template:probe:primer complex (TPP complex) and thus ensures that primer extension and template completion does not occur in the absence of template-bound probe whereby no fluorescence would be generated. The sequences of all templates, primers and probes are given in Table 1.

Example 10

Polymerase Selection

In contrast to previous template-based polymerase assays that quantify dNTPs, the design of this assay necessitates the use of a DNA polymerase with inherent 5' to 3' exonuclease activity to cleave the fluorophore-labeled probe during successful polymerization and nascent strand synthesis. In addition, one major drawback in previous polymerase-based assays using Klenow polymerase was the potential for mis-incorporation of rNTPs leading to artificially elevated measurements particularly for dGTP and dCTP. This was an important assay design consideration as rNTPs can be present in cell extracts (quiescent cells in particular) in molar ratios 1000-fold greater than their corresponding dNTP. Taq polymerase is reported to be 30,000-fold more efficient at discriminating between ribo- and deoxyribonucleotides (300,000 in the case of dTTP and UTP) primarily due to a single Glu-615 residue that can sterically exclude the 2'-OH of an incoming rNTP. A recent report identified Taq polymerase as having a 10-fold higher capacity to discriminate dNTPs from rNTPs than the commonly utilized Klenow DNA polymerase and demonstrated no significant interference from rNTPs even at the extremes of physiological rNTP concentrations. In addition to its dNTP discriminatory capabilities, the utilization of AmpliTaq Gold DNA polymerase that requires a 'hot-start' has a number of important advantages in this assay. The inactivity of the enzyme before the hot-start allows flexibility in the reaction setup, including pre-mixing of the reagents (including Taq polymerase addition) at room temperature. This was confirmed empirically by performing plate setup on ice (3° C.) versus room temperature (22° C.) with no significant variation in assay performance observed (data not shown). Secondly, the hot-start also serves as an efficient DNA denaturation step after which the ramp down to 60° C. facilitates the sequential binding (based on calculated Tm) of the probe followed by the primer to form the functional TPP complex. In addition, Taq polymerase inactivity during set-up and the first temperature ramp of the assay ensures that the timing of the reaction can be tightly controlled for all individual reactions and replicates and that mis-primed primers are not extended at temperatures where sub-optimal primer annealing may occur. At the 60° C. temperature in this assay and under optimum conditions, Taq polymerase demonstrates approximately 50% maximum polymerization activity with 1 U catalyzing the incorporation of 5 nmol of dNTP into acid insoluble product in 30 min at 60° C.

Example 11

Validation of Assay Principle and Performance

Figure 2:
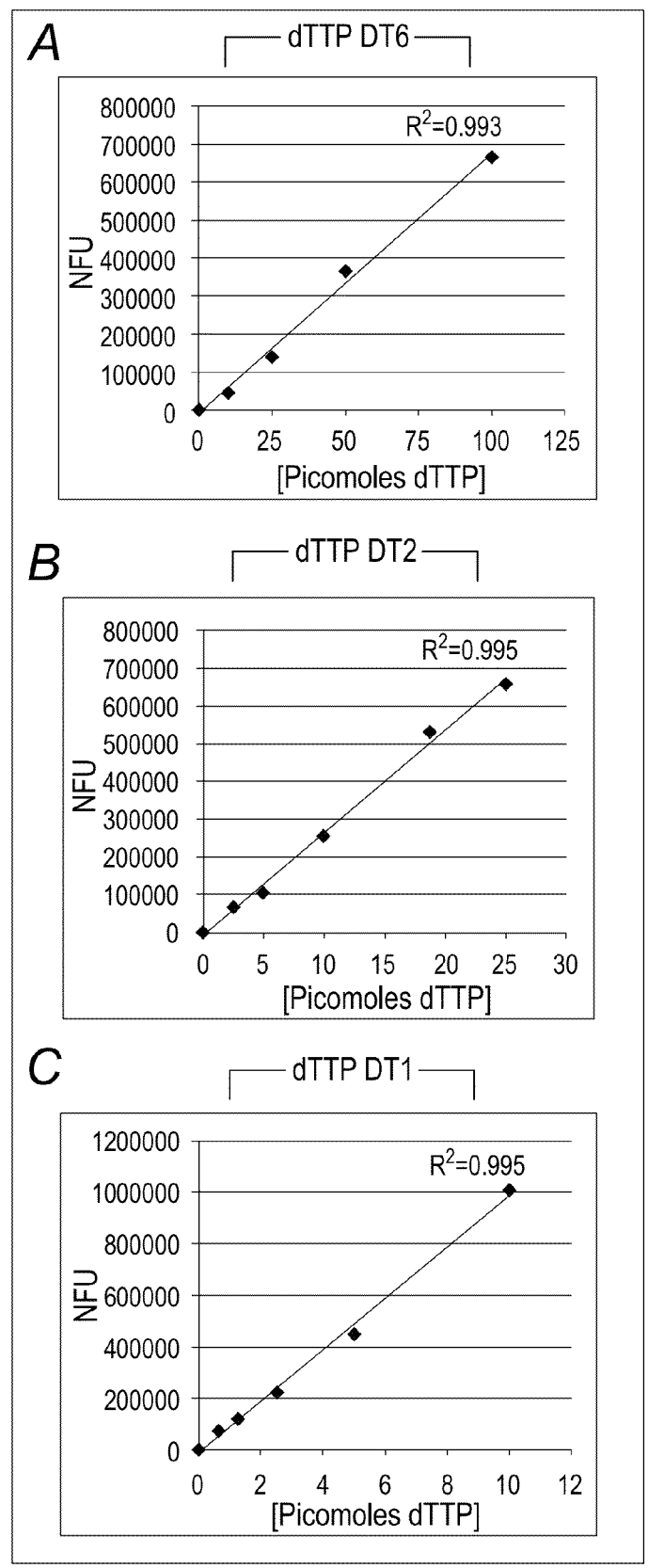
FIG. 2 demonstrates, in accordance with an embodiment of the invention, validation of dTTP templates with varying detection sensitivities and linear ranges. Three specific oligonucleotide templates were initially generated and tested for their ability to detect dTTP and tested by calibration curves as described herein. A. dTTP-DT6 requires the incorporation of 6 dTTPs for fluorescence generation and yielded a linear range of 0-100 pmoles. B. dTTP-DT2 requires the incorporation of 2 dTTPs and yielded a linear range of 0-25 pmoles. C. Finally, dTTP-DT1 requires only a single dTTP for incorporation per TPP complex to yield fluorescence and had a linear range of 0.6-10 pmoles. Calibration curves for all 3 templates demonstrated $R^2$ of >0.993. In all cases, fluorescence values for blank reactions (limiting dNTP omitted) were subtracted to give normalized fluorescence units (NFU).
Figure 3:
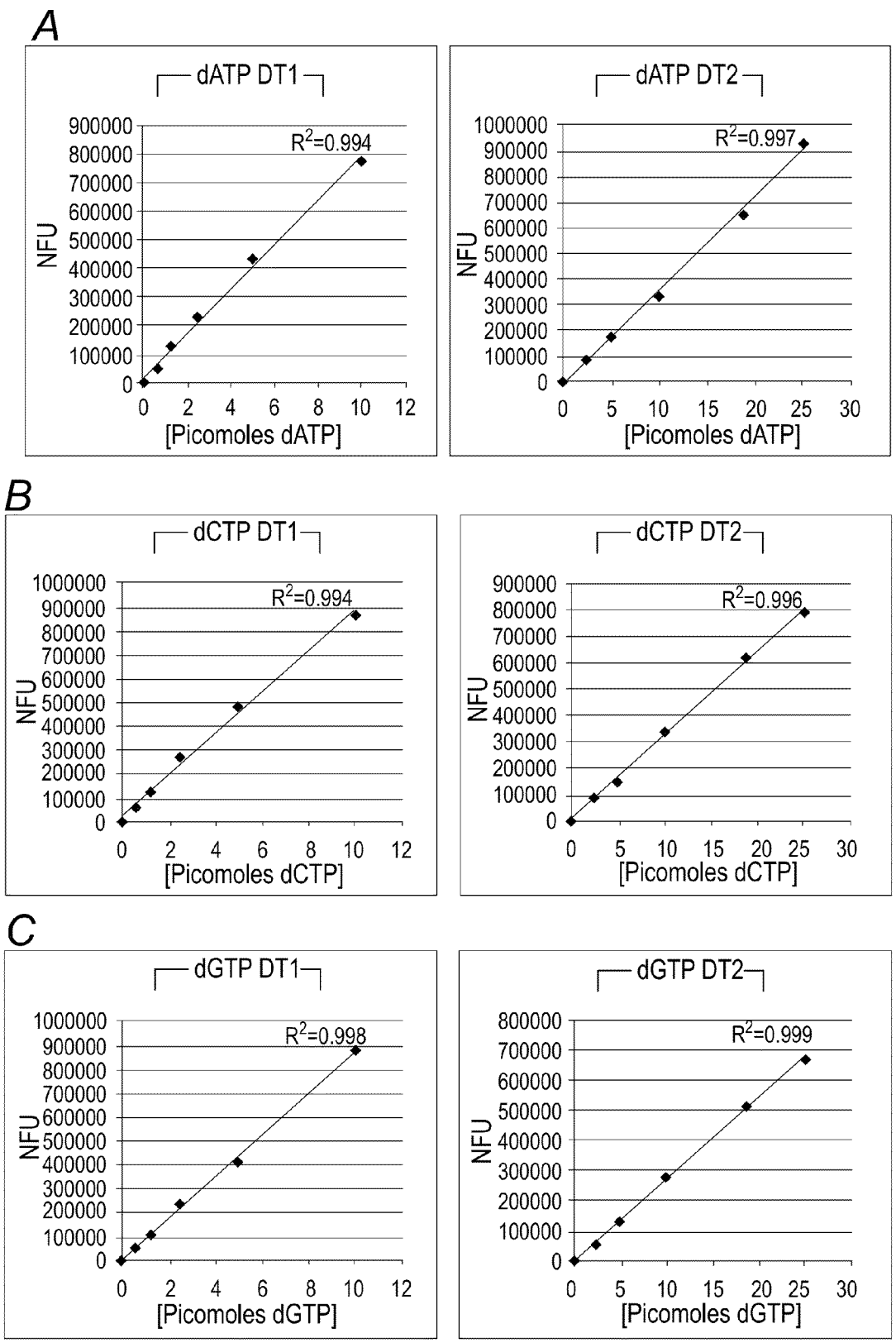
FIG. 3 demonstrates, in accordance with an embodiment of the invention, validation of dATP, dCTP and dGTP detection templates. Calibration curves were generated for dNTPs using dNTP-specific templates, DT1 and DT2, and probes (Table 1) and were performed as described herein. In all cases, fluorescence values for blank reactions, limiting dNTP omitted, were subtracted to give normalized fluorescence units (NFU). All curves demonstrated $R^2$ of >0.99. A. dATP, B. dCTP, C. dGTP. Left; DT1, Right DT2.

Initially, dTTP-DT6, -DT2 and -DT1 were all evaluated in the assay for their ability to detect dTTP. The raw fluorescence units obtained after 10 minute incubation were normalized to account for background probe fluorescence that was determined from controls lacking the limiting dNTP. The resulting normalized fluorescence units (NFU) obtained from serial dilutions of dTTP were utilized to generate calibration curves. Consistent with the design hypothesis, dTTP-DT6, which requires 6 dTTP incorporations per TPP complex to yield fluorescence, demonstrated excellent linearity and facilitated robust detection in the assayed range between ~10 and 100 pmoles of dTTP. dTTP-DT2, which requires 2 dTTP incorporation events for extension, also demonstrated excellent linearity in the assayed range between ~2.5 and 25 pmoles of dTTP. Finally, dTTP-DT1 which requires only a single dTTP incorporation event to yield fluorescence, demonstrated excellent linearity in the assayed range between 0.6 and 10 pmoles (~31-500 nmol/L) of dTTP. Calibration curves for all 3 dTTP DTs demonstrated excellent linearity with $R^2>0.99$ in every case (FIG. 2). Subsequent analysis of the remaining dNTPs (dATP, dCTP and dGTP) was performed using their corresponding DT1 and DT2. DTs for all dNTPs evaluated resulted in $R^2>0.99$ in every case and each yielded similar detection ranges and NFU under the same assay conditions (FIG. 3).

Example 12

Assay Sensitivity, Precision, Accuracy and Recovery

The mean LOD, which represents the smallest concentration or quantity of an analyte that can be reliably shown to be present or measured under assay conditions was investigated. The LOD was calculated from the standard curve as the mean value of the negative control plus 3 SD from three identical, inter-day assays and was determined to be 0.46±0.02 pmoles for dTTP, 0.77±0.5 for dATP, 0.3±0.16 for dCTP and 0.38±0.11 for dGTP (Table 2). The LOQ, defined as the mean value of the negative controls plus 5 SD from three independent assays, was determined by standard curve to be 0.88±0.15 pmoles for dTTP, 1.3±0.1 for dATP, 0.77±0.2 for dCTP and 0.81±0.01 for dGTP (Table 2).

The variability of the assay was evaluated by calculating the inter- and intra-assay co-efficients of variation (% CV) as described herein. The intra-assay coefficients of variation (% CVs) were determined to be 3.4±0.85 for dTTP, 3.64±1.2 for dATP, 4.04±0.63 for dCTP and 4.58±0.77 for dGTP. The interassay CV for dTTP was 8.5±6.3 for dTTP, 6.5±2.6 for dATP, 9.6±2.3 for dCTP and 4.1±3.5 for dGTP (Table 2).

Accuracy was determined in the low- and high-assay range and was within 100±15% for all dNTPs (Table 2). Recoveries were determined by obtaining the result from an undetermined cell extract spiked with a known quantity of a dNTP standard and comparing that to the sum of the individual results obtained for the dNTP standard and the extract determined separately. The assay method gave high recoveries within 100±7% for all dNTPs (Table 2).

Example 13

Progression of the Polymerase Reaction

Figure 4:
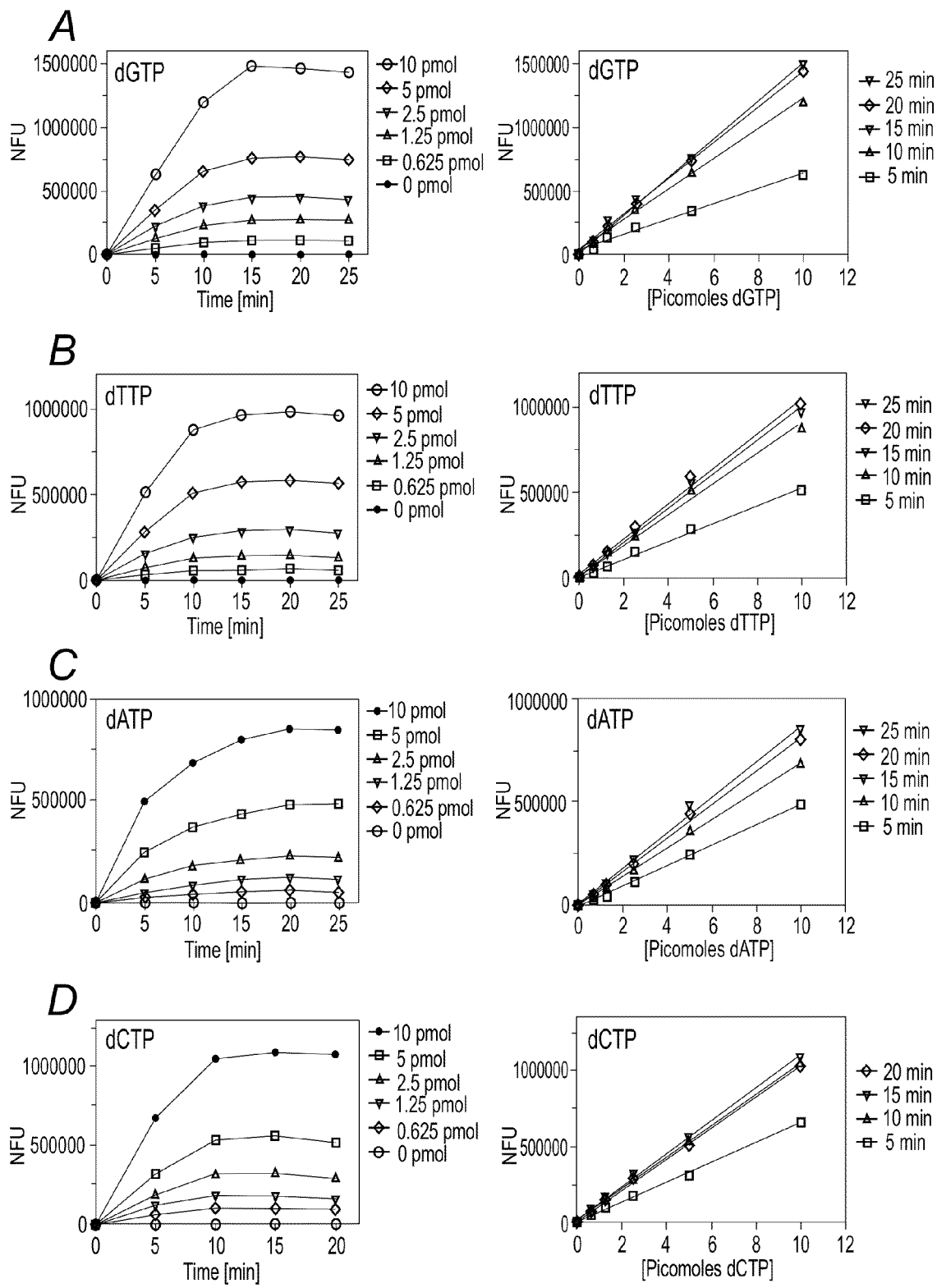
FIG. 4 demonstrates, in accordance with an embodiment of the invention, time-course and calibration curve analysis of the polymerase reaction. Time course showing fluorescence generated by the dNTP-dependent Taq DNA polymerase-mediated hydrolysis of a dual-quenched fluorescent-labeled probe. Lett. Known pmole quantities of dNTP were detected using DT1 and fluorescence was analyzed at 5 minute intervals on board an Applied Biosystems 7500 Real-Time PCR System. Right. Calibration curves were generated and plotted from the normalized fluorescence units obtained at the specified time intervals and analyzed by linear regression. All calibration curves demonstrated $R^2$ of >0.99. A. dGTP. B. dTTP. C. dATP. D. dCTP. Additional details of the assay are described herein.

Having demonstrated the feasibility of a fluorescence-based approach to detect and quantify low pmole quantities of dNTPs, the assay was optimized to determine improved conditions for the detection and quantification of intracellular dNTPs. As the assay was performed on an Applied Biosystems 7500 Real-Time PCR System, the real-time monitoring and fluorescence data-capture over specified 5 min time intervals was evaluated to monitor the progress of the polymerase reaction to completion. The generation of fluorescence with DT1 was rapid and robust with an incubation time of as little as 5 min necessary for the generation of calibration curves with good signal to noise ratio and excellent linearity ($R^2>0.99$). All subsequent time-points analyzed also showed excellent linearity indicating that the polymerase reaction is progressing in a linear manner and that substrate saturation has not occurred and the polymerase is below $V_{max}$. However, while linear calibration curves could be generated for all dNTPs with a 5 min incubation period, the polymerase reaction was not driven to completion (maximum DNA synthesis) until approximately 15 min for dGTP, dCTP and dTTP and 20 min for dATP (FIG. 4). However, for all dNTPs the NFUs obtained, and subsequent calibration curves generated at the later time-points of 20 and 25 min remained virtually identical to those obtained at 15 min with $R^2>0.99$ in every case (FIG. 4). While not wishing to be bound by any one particular theory, considering the potential for the presence of inhibitory molecules in cell extracts that may reduce assay kinetics, these later time-points should facilitate the accurate quantification of dNTPs from cell extracts where the assay has reached completion.

Example 14

Evaluating Assay Interference from Ribonucleotides

Figure 5:
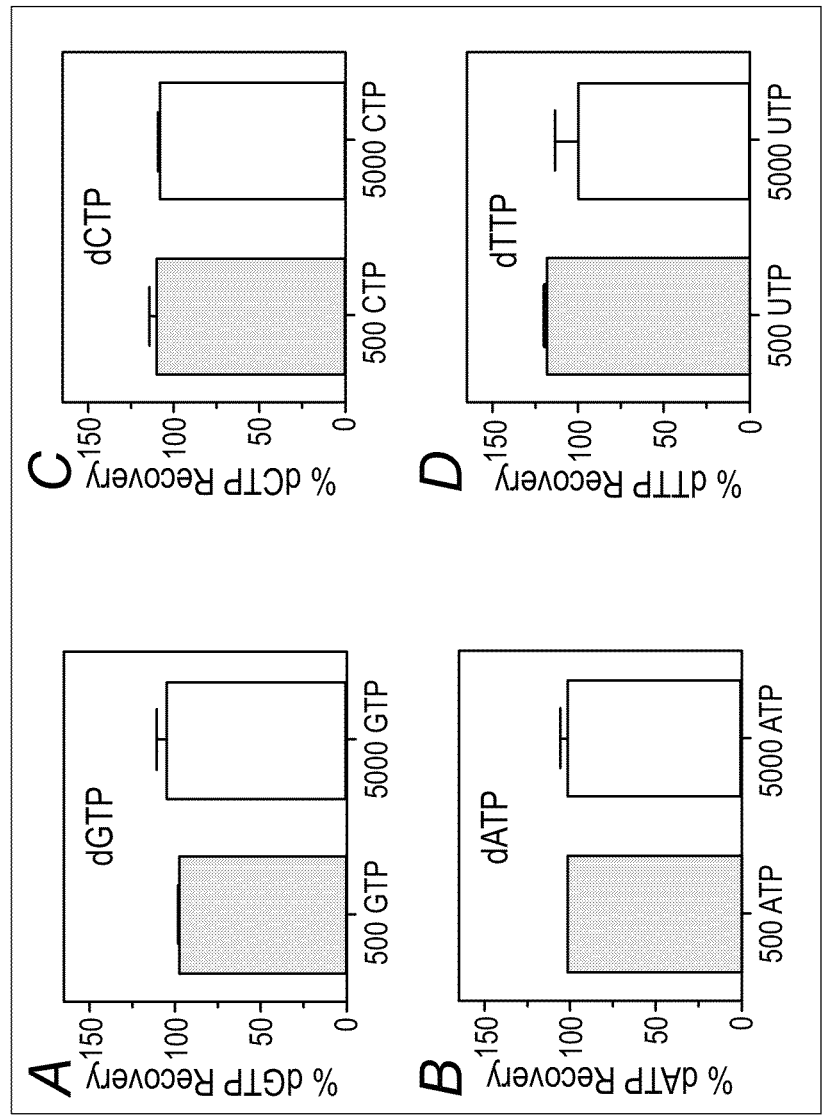
FIG. 5 demonstrates, in accordance with an embodiment of the invention, the effect of a 100- and 1000-fold molar rNTP excess on the recovery of dNTPs in the fluorescence-based assay with Taq polymerase. (A) The recovery of 5 pmoles of dGTP was determined in the presence of both a 100- and 1000-fold molar excess of GTP at assay completion (20 min). The same analysis was applied to the recovery of (B) dATP, (C) dCTP and (D) dTTP in the presence of their corresponding rNTP. Bars represent the mean±SD of three individual analyses. The assay was performed as described herein. In all cases, fluorescence values for blank reactions (limiting dNTP omitted) were subtracted to give normalized fluorescence units (NFU).

It has been well established that DNA polymerases have imperfect dNTP selectivity both in vitro and in vivo. Therefore one potential source of interference in the detection of intracellular dNTPs is from endogenous rNTPs. Although kinetic studies have revealed that Taq polymerase in particular is reported to be highly efficient at discriminating between rNTP and dNTPs, the potential for rNTP misincorporation resulting in overestimation of dNTP recovery in the present assay was tested. The inventors measured the recovery of 5 pmoles of dNTP in the presence and absence of 100- and 1000-fold molar excess of the corresponding rNTP and followed the assay in 5 min intervals to completion. A 100-fold molar excess of rNTP did not result in any significant increase in the recovery of the corresponding dNTP. Similarly, a 1000-fold molar excess of rNTP did not induce any increases in dNTP recovery (FIG. 5). Interestingly, while no evidence of significant rNTP misincorporation was evident, the presence of a 1000-fold molar excess of rNTPs demonstrated a mild inhibitory effect on assay kinetics. Specifically, the analysis of dGTP and dTTP recovery at the earlier time-points of 5 and 10 min indicated the presence of a weak competitive effect of a 1000-fold rNTP molar excess and reduced assay kinetics resulting in a reduced recovery of dGTP and dTTP calculated at those time points. However, the effect was transient and no evidence of rNTP-mediated assay inhibition (or activation) was observed for any of the dNTPs at the later time-points of 15 and 20 min upon assay completion.

Example 15

Determination of Intracellular dNTP Pools

The present invention was used to analyze the nucleotide pool content of the human colon cancer cell line HCT116 in log-phase growth and following treatment with anti-neoplastic agents known to perturb dTTP biosynthesis. The fluoropyrimidines fluorodeoxyuridine (FUdR) and 5-fluorouracil (5-FU) and the antifolate pemetrexed are anti-neoplastic chemotherapeutics that inhibit DNA synthesis through inhibition of thymidylate synthase (TS), resulting in depletion of dTMP an essential precursor to dTTP synthesis. Cells were incubated with vehicle or 1 µmol/L FUdR, 2.5 µmol/L pemetrexed, or 5 µmol/L 5-FU for 4 hours and processed for analysis as described herein. All dNTPs were successfully detected and quantified from cell extracts during normal log-phase growth (Table 3). Treatment with all three chemotherapeutics depleted dTTP pools as expected. Specifically, 1 µmol/L FUdR depleted dTTP >4-fold from 20.4 pmoles in vehicle-treated cells to 4.5 pmoles per $10^6$ cells while pemetrexed and 5-FU depleted dTTP down to 3.9 and 1.6 pmoles per $10^6$ cells respectively. In addition, while dATP showed no significant change, depletion of dGTP from 4.7 to 0.43, 1.1 and 0.9 pmoles per $10^6$ cells following treatment with FUdR, pemerexed and 5-FU respectively was observed. Reductions in dCTP levels from 10.5 to 8 and 8.7 pmoles per $10^6$ was observed following treatment with FUdR and 5-FU respectively (Table 3).

Example 16

Comparison to a validated LC-MS/MS assay for detecting dNTPs

Figure 9A:
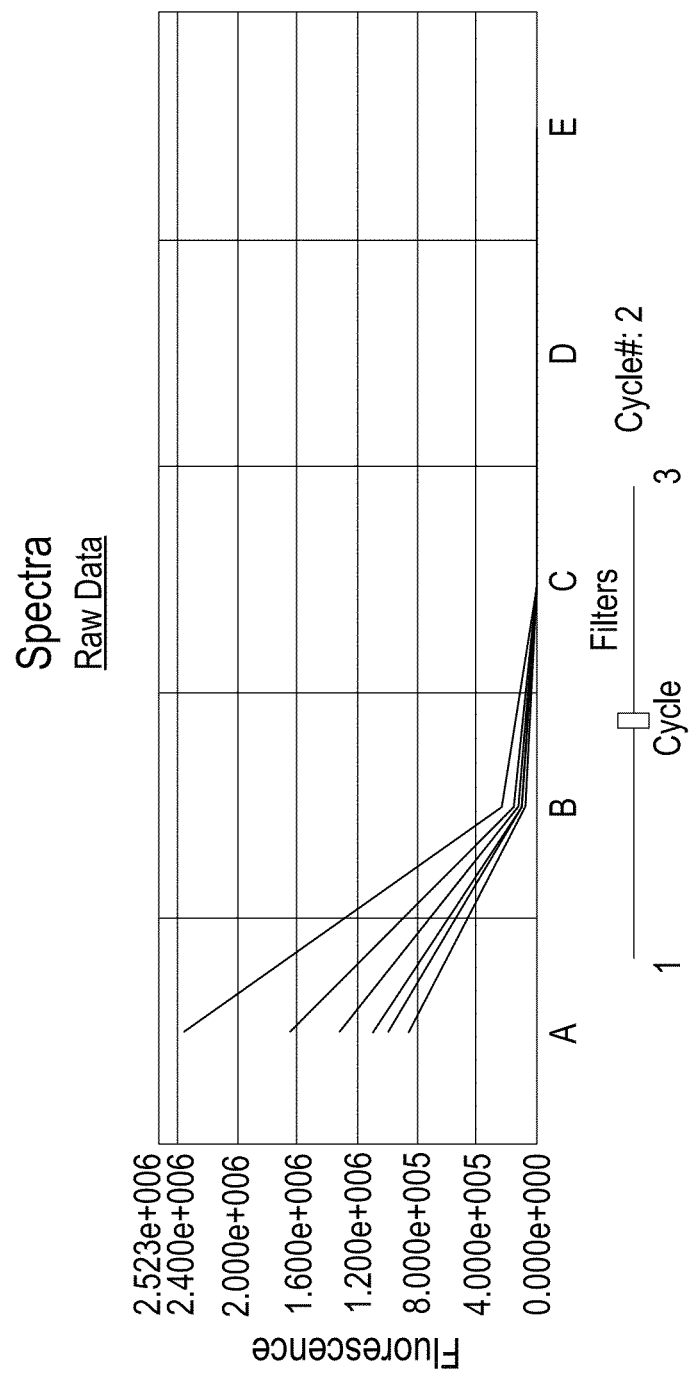
FIG. 9 demonstrates, in accordance with an embodiment of the invention, A. Raw fluorescence spectra visualized with SDS software user interface. Screenshot depicting the raw fluorescence spectra obtained for 6-FAM using Filter A generated from a calibration curve for dTTP (0-10 pmoles), as described herein. Raw fluorescence spectra is subsequently exported to MS Excel and analyzed by regression co-efficient. B. A LC-MS/MS-generated chromatograph. The chromatograph illustrates the intensity measured in counts per second (cps) and retention time for each dN (dephosphorylated dNTPs) and internal standards in the LC-MS/MS analysis.
Figure 9B:
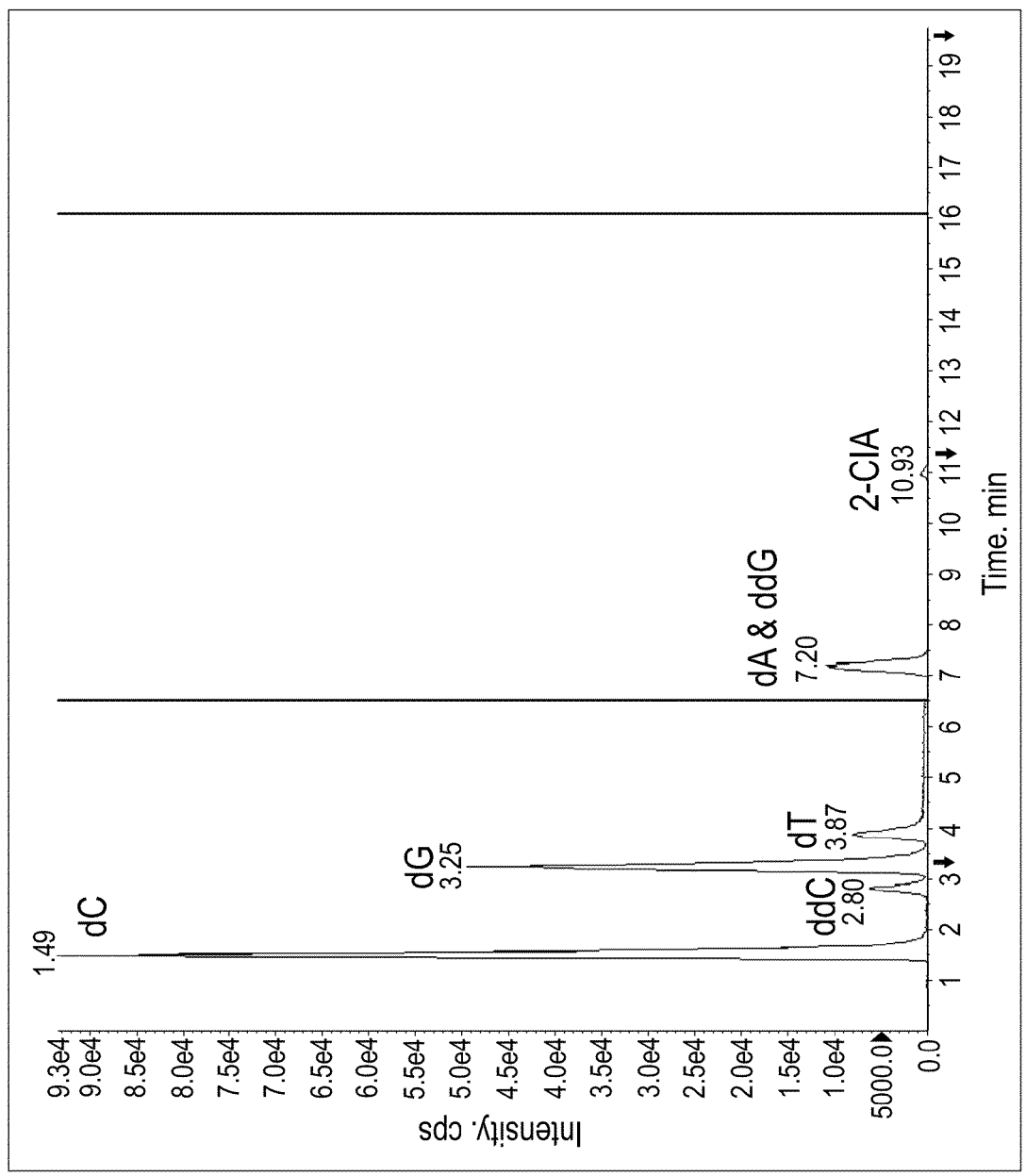

The inventors' enzymatic assay for quantifying cellular dNTPs was directly compared with results obtained from a previously validated LC-MS/MS-based assay performed by the Department of Clinical Pharmacy and Pharmaceutical Sciences at the University of Southern California. A known concentration of each dNTP was provided from which calibration curves were generated and the concentration of 3 biological extracts were determined by both assays in a blinded manner. The LC-MS/MS determination was performed as described herein. A chromatograph illustrating the intensity measured in counts per second (cps) and retention time for each dN (dephosphorylated dNTPs) and internal standards is given in FIG. 9. The results obtained for the unknowns by LC-MS/MS were directly compared to those determined in the current fluorescence-based polymerase assay and the difference between the two methodologies expressed as percent difference. Despite the differing methodologies, reagents and instrumentation involved, the assay results were in good agreement with mean±SD percent differences of −11±6% for dCTP, −14±5.9% for dGTP, −5.2±11.6% for dTTP and −4.5±13.4% observed for dATP between the two assays.

Example 17

Assay Modification to Detect dUTP

Figure 6:
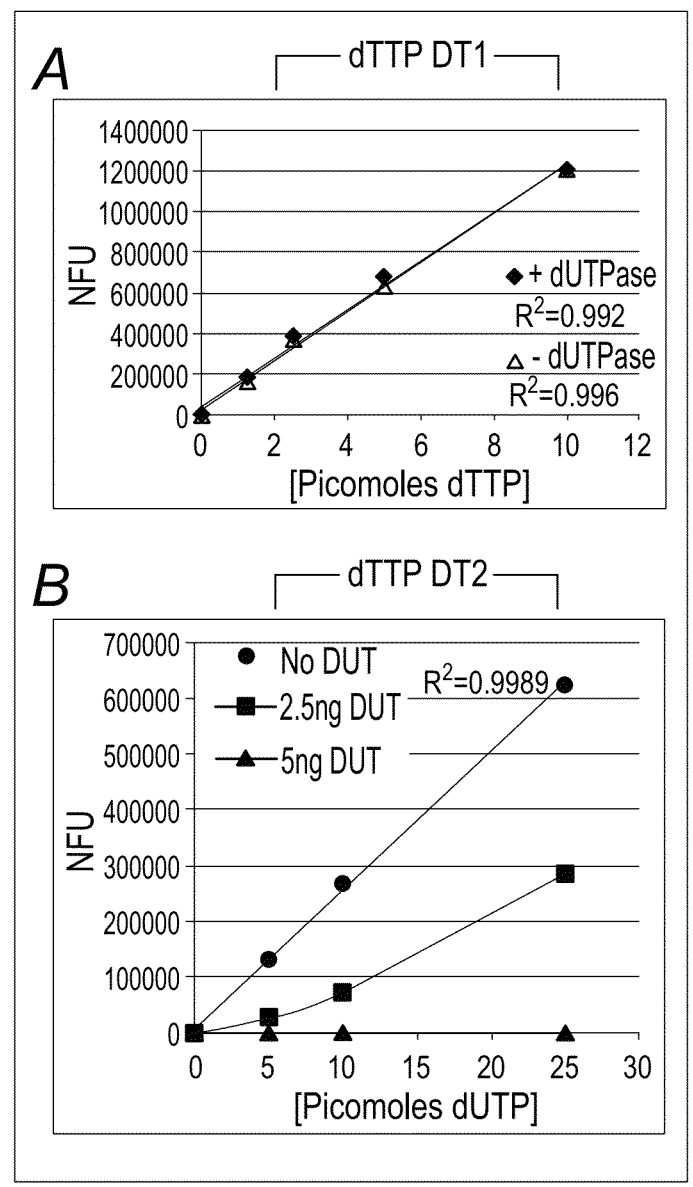
FIG. 6 demonstrates, in accordance with an embodiment of the invention, detection of dUTP. The ability of the assay to detect dUTP and distinguish dTTP from dUTP in the presence and absence of the dUTP-hydrolyzing enzyme dUTPase was analyzed. A. The effects of including recombinant human dUTPase (DUT) and a 5 min pre-incubation at 37° C. were first analyzed. Inclusion of 5 ng of dUTPase had no significant impact on the assay performance and detection of dTTP ($R^2$ of >0.99). B. dTTP was replaced with dUTP and the reaction performed in the absence of dUTPase and in the presence of 2.5 and 5 ng of recombinant human dUTPase. In the absence of dUTPase, dUTP detection was robust and yielded an excellent calibration curve ($R^2$ of >0.99). Five ng of dUTPase was sufficient to eliminate dUTP as the source of fluorescence in the assay whereas 2.5 ng resulted in partial hydrolysis and intermediate fluorescence. The assay was performed as described herein. In all cases, fluorescence values for blank reactions (limiting dNTP omitted) were subtracted to give normalized fluorescence units (NFU).
Figure 7:
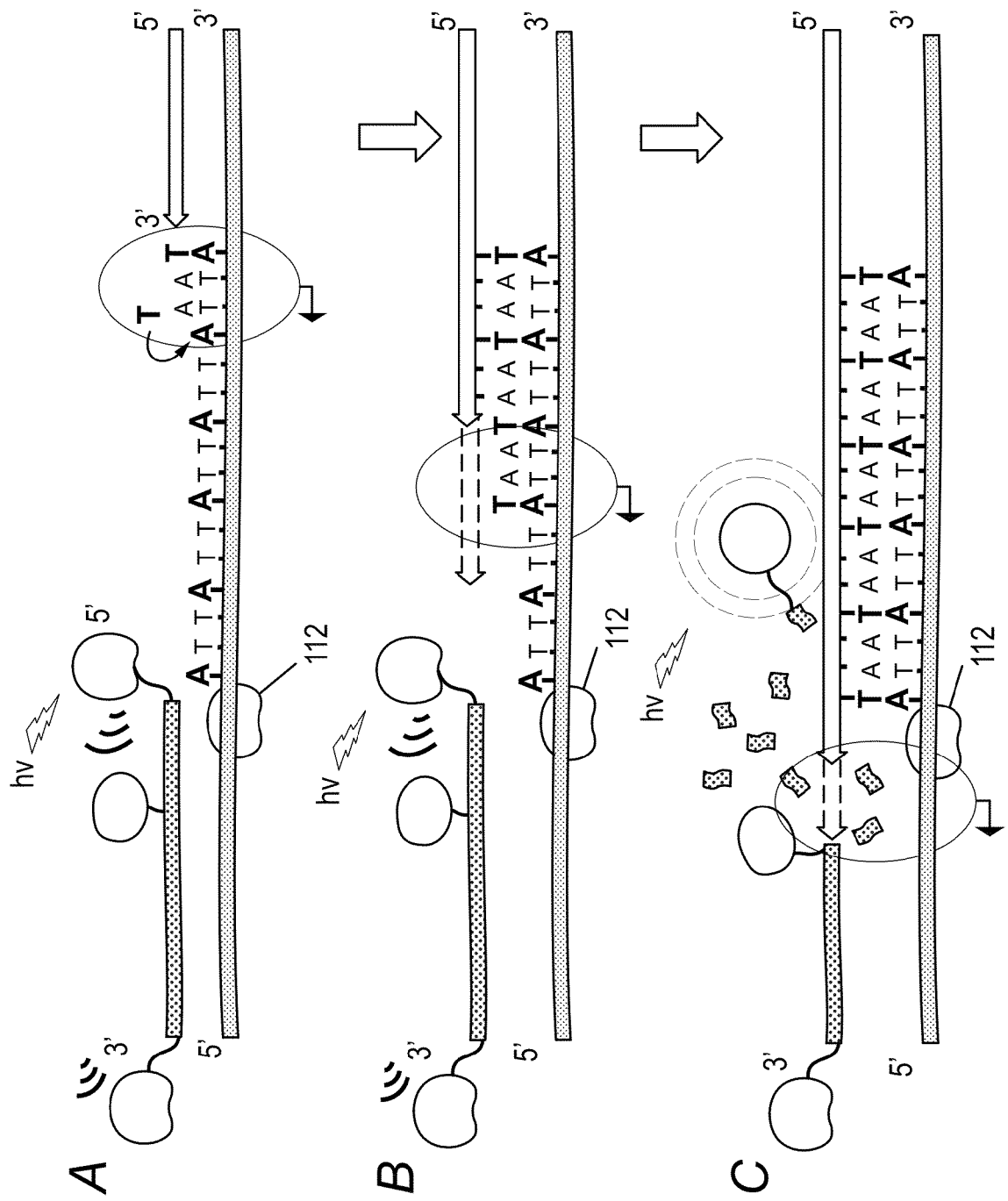
FIG. 7 demonstrates, in accordance with an embodiment of the invention, incorporation of a quencher nucleotide 112 into the template immediately opposite where the 5' end of the fluorophore-labeled probe hybridizes. This significantly increases the sensitivity of the assay through reduction in assay background and an increase in the linear range. The remaining elements of the drawing, including the sequences of SEQ ID NOs.: 15-18 within the template and nascent strand, are as described in FIG. 1.
Figure 8:
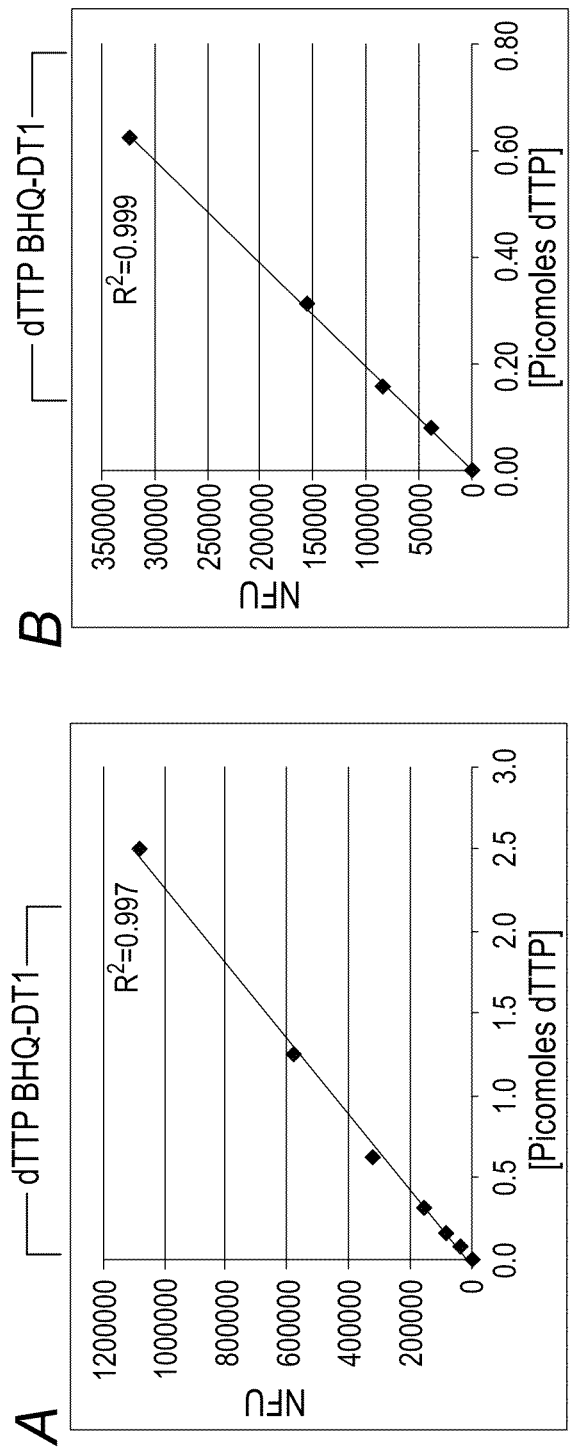
FIG. 8 demonstrates, in accordance with an embodiment of the invention, incorporation of a dt-BHQ-1 nucleotide into the template immediately opposite where the 5' end of the fluorophore-labeled probe hybridizes. This increases the sensitivity of the assay through reduction in assay background and an increase in the linear range. This figure demonstrates the ability to detect sub-picomole quantities of dTTP.

The nucleotide intermediate dUTP can be incorporated into newly synthesized DNA opposite dAMP in place of dTTP, therefore an additional application of this assay is the ability to measure dUTP. In applications measuring dTTP pool imbalance, such as those that employ chemotherapeutics targeting thymidylate metabolism, intracellular dUTP pools can accumulate in parallel with acute dTTP depletion and provide inaccurate results in polymerase-based assays. Therefore, in order to accurately determine the concentrations of dTTP, the presence of any contributing dUTP needs to be accounted for. The presence of dUTP can be efficiently determined and accounted for by performing parallel reactions with and without a pre-incubation with the enzyme dUTPase which catalyzes the hydrolysis of dUTP to dUMP and pyrophosphate and removes its availability for nascent strand incorporation. The dUTP pool concentration can thus be determined by subtracting the results of cell extracts treated with dUTPase from the untreated extracts. Importantly, the AmpliTaq Gold polymerase buffer II was conducive for excellent dUTPase enzymatic activity and complete hydrolysis of 25 pmoles of dUTP was observed with a 10 min incubation with 5 ng of dUTPase at 37° C. prior to initiation of the normal assay program. The inclusion of dUTPase in the assay reaction mix did not interfere with assay performance as evidenced by parallel reactions measuring dTTP with and without dUTPase that demonstrated excellent linearity ($R^2 > 0.99$) and were virtually identical (FIG. 6A). When dUTP was measured as the rate-limiting dNTP, excellent linearity was also recorded, however, partial digestion resulting in intermediate fluorescence was observed with 2.5 ng of dUTPase. Increasing the amount of enzyme to 5 ng of dUTPase per reaction completely hydrolyzed 25 pmoles yielding no fluorescence signal above background (FIG. 6B). This confirmed the specificity of the assay for the limiting dNTP (dUTP in this instance) and confirmed that the assay has the potential to be modified to accurately measure dUTP in addition to the canonical dNTPs.

Example 18

Discussion

The current assay is a novel fluorescence-based approach utilizing fluorescence technology to provide a rapid, sensitive and cost-effective alternative to current methodologies that necessitate the incorporation of radioactivity and/or HPLC and MS instrumentation for the detection of dNTPs. This assay was successfully applied to the detection of dATP, dTTP, dGTP, dCTP and dUTP in in vitro assays and in the quantification of intracellular dNTP pools from human cancer cells.

The current assay was validated in line with current FDA guidelines for analytical assays and demonstrated excellent accuracy, sensitivity, reproducibility and recovery within accepted guidelines. The current assay has several inherent qualities that make it more attractive and efficient than radiolabeling or HPLC and LC-MS/MS methods that are still currently in use. One limitation with conventional template-based DNA polymerase assays is the limited linear range up to 10 pmoles. To address this, the inventors designed and validated additional detection templates that allow detection of up to 60 pmoles of dNTP at assay completion thereby significantly expanding the linear detection range. For example, in assays were maximum sensitivity is required such as dNTP detection from low numbers of prokaryotic and eukaryotic cells, DT1 which requires only a single limiting dNTP incorporation event for fluorescence generation, would provide the most sensitive detection of low pmole quantities of dNTP. However, if an in vitro enzymatic screening assay is being performed and extreme sensitivity is not required, DT6 which requires 6 limiting dNTP incorporation events to yield fluorescence, would provide a broader range of linear detection (approx 5-60 pmoles at assay completion) and may be more suitable. The current assay has sufficient sensitivity for the majority of cell-based applications without the requirement for excessive or impractical cell numbers. The analysis of dNTP pools in cells not undergoing DNA replication, or the quantification of mitochondrial dNTP pools may represent a challenge for the current assay as these values may approach and exceed the limit of detection from an initial sample size of $10^6$ cells. Such analyses would thus require a larger initial sample size to facilitate accurate quantification. While not wishing to be bound by any one particular theory, it is likely that different probe designs and/or combinations of reporter and quencher molecules in the probe would facilitate an increase in sensitivity in the assay. Furthermore, although the fluorophore detection capabilities of real-time PCR platforms vary, numerous commercially available fluorophore and quencher combinations are available to suit the requirements of most platforms and applications and could be adapted to the FRET technology that this assay is based upon.

One additional advantage of the current assay over the conventional radiolabeled dNTP polymerase assays is that there is no interference in the current assay from the endogenous cellular dNTP corresponding to the radiolabeled dNTP substrate ([3H]dNTP) as previously reported. An additional issue with the radiolabeled assay is that the specific radioactivity of dNTPs in radioisotope experiments cannot be measured. The current assay circumvents this issue by avoiding the need for a radiolabeled dNTP and employing a fluorescence-labeled probe that demonstrates robust linearity. One key attribute of the current assay is the straightforward and uncomplicated assay set up. All reagents can be added and mixed at room temperature and the use of a 96-well-format real-time PCR instrument facilitates the simultaneous analysis of all dNTPs with the ability to monitor assay kinetics in real-time by acquiring fluorescence readings at multiple user-defined time-points to follow progression of the polymerase reaction and ensure analysis occurs at the most appropriate interval without the need to irreversibly terminate the polymerase reaction and extract the sample for downstream detection.

The current assay provides the ability to measure all four canonical cellular dNTPs on a single 96-well plate under identical assay detection conditions with the same DNA polymerase. In addition, the use of Taq polymerase in this assay also appears to significantly limit the potential for dNTP overestimation as a result of rNTP misincorporation.

The current assay is extremely rapid with the final detection step requiring approximately ~30 min. If extraction of intracellular nucleotides is required, the entire protocol can be completed in less than 3 hours, including extraction and concentration of dNTPs, plate setup and final detection. The small reaction volume, low enzyme and probe requirement per reaction also make this a relatively inexpensive assay. The current assay was also directly compared to a validated LC-MS/MS-based approach for detecting and quantifying dNTPs and despite the distinct contrast in techniques, the results obtained for unknown samples were in good agreement.

The assay was also modified to measure the nucleotide intermediate dUTP (which can be utilized as a substrate by DNA polymerase) with excellent results. By performing the reaction with dUTP in the presence and absence of the dUTP-hydrolyzing enzyme dUTPase, both the flexibility of the assay and the substrate specificity was confirmed. As expected, a short pre-incubation with sufficient dUTPase completely eliminated fluorescence compared to the no-enzyme control for dUTP but not dTTP confirming the specificity of the limiting dNTP (dUTP) as the source of fluorescence generation in the assay.

The determination of intracellular dNTP levels is of fundamental importance in understanding the underlying biology of a number of genetic diseases and in determining the mechanisms of action of a wide range of pharmacological agents designed to perturb dNTP metabolism and DNA replication in both prokaryotic and eukaryotic organisms. This assay therefore has important and broad application in research measuring dNTPs and/or the activity and inhibition of enzymes directly or indirectly involved in dNTP biosynthesis. The accurate quantification of dNTP pools in response to anti-cancer agents that target dNTP biosynthesis represents one important application and was the primary motivating factor that led to the development of this assay. The inventors confirmed this application by successfully measuring perturbations in dTTP pools in human tumor cells as a result of inhibiting a key enzyme involved in dTTP biosynthesis. Treatment with FUdR, 5-FU and pemetrexed resulted in rapid perturbations in dNTP pools similar to those previously reported for both these agents. Specifically, measurable decreases in both dTTP and dGTP concentrations were observed. The intracellular dNTP concentrations obtained for tumor cells with the current assay were within 15-20% of previously published studies using similar models and conditions.

Another important attribute of this assay is its potential for adaptation to high-throughput applications (384-well and beyond), making it particularly amenable to high sample volumes or to the screening of pharmacological molecules that perturb dNTP metabolism either from cell-based assays or in vitro screening.

In summary, the fluorescence-based dNTP detection assay described in this invention represents a rapid, sensitive, reproducible and cost-effective alternative to current radiolabeling and HPLC and MS-based methodology to detect and quantify dNTPs.

Example 19

TABLE 1

Primer, probe and templates utilized in the assay

| Name | Classification | Sequence and SEQ ID NOs (5'-3') | Size bp | Tm[a] °C. |
|---|---|---|---|---|
| NDP-1 | Primer | SEQ ID NO: 1<br>CCGCCTCCACCGCC | 14 | 56 |
| FAM-dTTP Probe[†] | | SEQ ID NO: 2<br>*X*/AGGACCGAG/*Y*/GCAAGAGCGAGCGA/*Z* | 23 | 70 |
| dTTP-DT6 Template[§] | | SEQ ID NO: 3<br>TCGCTCGCTCTTGCCTCGGTCCTT*A*TT*A*TT*A*TT*A*TT*A*TT*A*GGCGGTGGAGGCGG | 54 | 69 |
| dTTP-DT2 Template[§] | | SEQ ID NO: 4<br>TCGCTCGCTCTTGCCTCGGTCCTTT*A*TTT*A*TTTGGCGGTGGAGGCGG | 47 | 72 |
| dTTP-DT1 Template[§] | | SEQ ID NO: 5<br>TCGCTCGCTCTTGCCTCGGTCCTTT*A*TTTGGCGGTGGAGGCGG | 43 | 73 |
| FAM-dATP Probe[†] | | SEQ ID NO: 6<br>*X*/TGGTCCGTG/*Y*/GCTTGTGCGTGCGT/*Z* | 23 | 68 |
| dATP-DT2 Template[§] | | SEQ ID NO: 7<br>ACGCACGCACAAGCCACGGACCAAA*T*AAA*T*AAGGCGGTGGAGGCGG | 47 | 73 |
| dATP-DT1 Template[§] | | SEQ ID NO: 8<br>ACGCACGCACAAGCCACGGACCAAA*T*AAAGGCGGTGGAGGCGG | 43 | 74 |
| FAM-dCTP Probe[†] | | SEQ ID NO: 9<br>*X*/AGGATTGAG/*Y*/GTAAGAGTGAGTGG/*Z* | 23 | 63 |
| dCTP-DT2 Template[§] | | SEQ ID NO: 10<br>CCACTCACTCTTACCTCAATCCTTT*G*TTT*G*TTTGGCGGTGGAGGCGG | 47 | 70 |
| dCTP-DT1 Template[§] | | SEQ ID NO: 11<br>CCACTCACTCTTACCTCAATCCTTT*G*TTTGGCGGTGGAGGCGG | 43 | 70 |
| FAM-dGTP Probe[†] | | SEQ ID NO: 12<br>*X*/ACCATTCAC/*Y*/CTCACACTCACTCC/*Z* | 23 | 64 |
| dGTP-DT2 Template[§] | | SEQ ID NO: 13<br>GGAGTGAGTGTGAGGTGAATGGTTT*C*TTT*C*TTTGGCGGTGGAGGCGG | 47 | 71 |
| dGTP-DT1 Template[§] | | SEQ ID NO: 14<br>GGAGTGAGTGTGAGGTGAATGGTTT*C*TTTGGCGGTGGAGGCGG | 43 | 71 |

[a] Tm calculated in presence of 50 mmol/L NaCl.
[†] Letters in bold and italics denotes the type and location of probe modifications, wherein X is 6FAM, Y is Zen and Z is IBFQ.
[§] Bases in bold and italics represent the dNTP to which the limiting dNTP will base pair opposite.

Sequence IDs do not include elements X, Y and Z described above.

Example 20

TABLE 2

Assay performance results for each dNTP determined from DTI

| dNTP | Regression coefficient | % Accuracy* Low, High | LOD$^\ominus$ (pmoles) | LOQ$^\dagger$ (pmoles) | Interassay % CV | Intrassay % CV | % Recovery |
|---|---|---|---|---|---|---|---|
| dTTP | >0.995 | 114.9 ± 6, 101.4 ± 5.3 | 0.46 ± 0.02 | 0.88 ± 0.15 | 8.5 ± 6.3 | 3.4 ± 0.85 | 103.6% |
| dGTP | >0.998 | 98.9 ± 11.7, 95.6 ± 8.2 | 0.38 ± 0.1 | 0.81 ± 0.01 | 4.1 ± 3.57 | 4.58 ± 0.77 | 103.3% |
| dATP | >0.994 | 100.5 ± 13.3, 101.6 ± 7.7 | 0.77 ± 0.5 | 1.3 ± 0.1 | 6.5 ± 2.6 | 3.64 ± 1.2 | 93.2% |
| dCTP | >0.994 | 101.6 ± 14.7, 100.3 ± 5.26 | 0.36 ± 0.16 | 0.77 ± 0.2 | 9.6 ± 2.3 | 4.04 ± 0.63 | 96.4% |

*Accuracy was calculated in the low-mid and mid-high assay ranges.
$^\ominus$LOD; limit of detection.
$^\dagger$LOQ; limit of quantification.

Example 21

TABLE 3

Intracellular dNTP concentrations determined from HCT116 human colorectal cancer cells treated with fluoropyrimidine-based thymidylate synthase inhibitors FUdR and 5-FU and the antifolate pemetrexed

| | pmoles × $10^6$ cells* | | | |
|---|---|---|---|---|
| dNTP | Control | 1 μmol/L FUdR | 2.5 μmol/L PTX | 5 μmol/L 5-FU |
| dATP | 13.6 ± 1.17 | 14.5 ± 0.13 | 13.4 ± 1.68 | 13.9 ± 0.33 |
| dCTP | 10.5 ± 0.2 | 8 ± 0.04 | 11.1 ± 2.5 | 8.7 ± 0.24 |
| dGTP | 4.7 ± 0.8 | 0.43 ± 0.11 | 1.14 ± 0.3 | 0.88 ± 0.1 |
| dTTP | 20.4 ± 0.77 | 4.5 ± 0.71 | 3.93 ± 0.8 | 1.64 ± 0.16 |

*Values represent the Mean ± SD determined from two independent isolations analyzed in duplicate. Cells were treated for 4 h with vehicle (sterile ddH$_2$0 or DMSO) or with the specified concentrations of PTX; pemetrexed, FUdR; fluorodeoxyuridine, 5-FU; 5-fluorouracil.

Example 22

Universal Method

The following protocol provides a universal method suitable for the detection of all dNTPs as described herein. (1) Reconstitute all oligonucleotides including primer, probe and templates in sterile, nuclease-free water at a stock concentration of 100 μmol/L. Generate working stocks of each of these at 10 μmol/L. See Notes 1-3 for additional guidance on reagent preparation. (2) Thaw all reagents on ice. Retain the AmpliTaq DNA polymerase at −20° C. until immediately prior to use. (3) Calculate the number of analyses required and scale-up PCR master mix as appropriate. Refer to Note 4 for the final concentrations of each component in a single reaction. One 25 μl reaction contains the following components (stock concentrations are in parentheses): *Volume: Component: Stock concentration*—1 μl of primer NDP1 (10 μmol/L), 1 μl of selected template (10 μmol/L), 1 μl of selected probe (10 ninon), 2 μl of MgCl$_2$ (25 mmol/L), 1 μl of dNTPs (2.5 mmol/L), 2.5 of 10×PCR Buffer II, 0.175 μl of AmpliTaq Gold Polymerase (5 U/μl), 14.825 μl of nuclease-free H$_2$0 to a final volume of 22.5 μl. See Note 5. (4) Aliquot 22.5 μl to each well on a 96-well PCR plate and add 2.5 μl of dNTP standard or extract to the appropriate wells. See Note 6. (5) Once plate setup is complete, seal the 96-well plate and spin briefly at 3000 g to ensure all contents are at the bottom of the wells. Transfer the plate to the real-time PCR thermocycler. Program the real-time PCR thermocycler to detect the 6-FAM fluorophore and select the wells to be analyzed using the thermocycle software. See Note 7. (6) Program the thermocycler to perform 3 steps: The first step is a one-time 10 min step at 95° C. to hot-start the polymerase, the second is a 5 min 60° C. incubation step during which the polymerization occurs, the third step is a fluorescence plate-read at the conclusion of each 5 min incubation step. The incubation and plate-read steps can be repeated for a minimum of 8 cycles (40 min total). This will allow real-time analysis of assay progression and kinetics in 5 min cycles up to 40 mins at which point the reaction should be complete. (7) Although real-time PCR platforms vary, all commercially available platforms currently in use will allow detection of the 6-FAM fluorophore and will facilitate the raw fluorescence spectra to be exported. Unlike real-time PCR, the generation of $C_T$ values is not applicable since this polymerization is not cyclic and the data is therefore analyzed differently. The raw fluorescence spectra for each well should be the only data exported and analyzed. See Note 8. (8) Data analysis consists of generating normalized fluorescence units (NFUs) by subtracting the fluorescence units for the negative control or 'zero pmole' standard from all other generated values. The NFUs for the standards should be plotted to generate a calibration curve from which the concentration of unknowns can be calculated. If data from multiple time-points has been captured, see Note 9.

Example 23

Assay Notes (1) Ensure that all oligonucleotides are PAGE-purified and have a specific guaranteed full-length yield. Probes are typically HPLC-purified, (2) Aliquot the FAM-labeled probes to avoid repeated freeze/thaws; a 100 μl aliquot (10 μmol/L) is sufficient for 100 reactions or approximately one 96-well plate. (3). The dNTP mix excludes the dNTP to be assayed. Therefore, a separate dNTP mix is required for the detection of each of the canonical dNTPs. For example, to detect dTTP a dNTP mix consisting of 100 μl of stock concentrations of 10 mmol/l dATP, 100 μl of dCTP, 100 μl of dGTP and 100 μl of sterile nuclease-free water will yield 500 μl of a dC/G/ATP dNTP mix at 2.5 mmol/L ready for use in the assay to detect dTTP. The exclusion of the dNTP to be assayed is important for assay success. (4) In a typical 25 μl reaction, the primer, template and probe are at an equimolar final concentration of 0.4 μmol/L. MgCl$_2$ is at a final concentration of 2 mmol/L, dNTPs are at a final concentration of 100 µmol/L, and 0.175 µl of AmpliTaq equates to 0.875 U of polymerase per reaction. (5) The volume of nuclease-free H$_2$O can be modified to accommodate between 1 and 5 µl of extract to be analyzed to determine linearity or to ensure the dNTP concentration is within the linear detection range. The example given utilized a 2.5 µl sample volume. Sample volumes of less than 1 µl are not recommended for pipetting accuracy reasons. (6) The mastermix and plate setup does not have to be performed on ice since the polymerase is inactive prior to hot-start, however, adding the AmpliTaq last is recommended. (7) The 6-FAM fluorophore (5'-carboxyfluorescein) has an excitation max of 494 nm and an emission max of 520 nm, most real-time thermocyclers will allow the user to manually create a detector programmed with the above excitation and emission wavelengths. (8) In the case of the Applied Biosystems Sequence Detection Software (V.1.4), data exportation can be achieved at the conclusion of the run by selecting File→Export→Spectra which yields the option to name and save the exported fluorescence units as a .csv file (MS Excel) to the selected location. The .csv file can be subsequently saved as a .xls or other common MS Excel format once opened in MS Excel. (9) The analysis of multiple time-points generates an abundance of data. However, with MS Excel it is possible to analyze multiple assay time-points simultaneously and as such, the analysis should take no longer than a single data-set. To do this, the fluorescence spectra pertaining to each time-point should be cut from the original ,csv and pasted into its own separate tab within a new excel worksheet ensuring that the replicate timepoint data are pasted into the exact same identical cell positions. Multiple tabs can thus be selected and the data analyzed for each time-point simultaneously.

Example 24

Ensuring Good PCR Laboratory Practice

Although this assay differs from conventional PCR in that the template can be supplied by the user in known quantities and the reaction is not cyclic, the basis of the reaction remains the polymerase-catalyzed synthesis of DNA and as such standard precautions should be observed during assay and sample preparation as would be observed with conventional PCR. In particular, contamination with DNAses or exogenous dNTPs (even in extremely low quantities) will compromise the assay. Care must be taken at all times to ensure that contamination with interfering molecules does not occur. The following guidelines should reduce the potential for any such contamination. Wear clean gloves and a clean lab coat. Use certified sterile, DNA- and RNAase-free microfuge tubes. Change gloves whenever it is suspected that they are contaminated. Maintain separate areas and dedicated equipment and supplies for: sample preparation, plate setup and data analysis. Open and close all sample tubes carefully. Avoid splashing PCR samples or components. Even trace contamination of components with the limiting dNTP will compromise the assay, Keep reactions and components capped as much as possible. Alternatively, the use of a PCR hood is strongly encouraged. Use a positive-displacement pipette and DNAse-free barrier-pipette tips. Clean lab benches and equipment periodically with 70% ethanol or 10% bleach solution. Ensure that the detection platform is calibrated and within acceptable detection parameters for the 6-FAM fluorophore. This can be achieved by utilizing manufacturer spectral calibration and region-of interest calibration plates. Calibration of the detection instrument will limit background, enhance the assay dynamic range and ensure optimum assay performance.

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A method for quantifying a particular deoxyribonucleoside triphosphate (dNTP) in a sample, comprising: providing an oligonucleotide template specific for the particular dNTP, comprising a 3' primer binding region adjacent to a dNTP detection region and a 5' fluorophore-labeled probe binding region adjacent to the dNTP detection region; hybridizing a fluorophore-labeled probe to the fluorophore-labeled probe binding region and hybridizing a primer to the primer binding region, whereby a template primer probe (TPP) complex is formed, and wherein the fluorophore-labeled probe comprises a fluorophore and one or more quenching molecules, wherein the one or more quenching molecules quenches a fluorescence from the fluorophore in the absence of the particular dNTP; providing a polymerase; combining the TPP complex to which the polymerase is bound with the sample, whereby primer extension and polymerase-mediated 5'-3' exonuclease hydrolysis of the fluorophore-labeled probe ensues if a sufficient quantity of the particular dNTP is present in the sample; exciting the fluorophore; detecting a resulting fluorescence; and quantifying the particular dNTP in the sample, based upon the resulting fluorescence.

2. The method of claim 1, wherein one or more of the quenching molecules is a non-emissive (dark) quenching molecule selected from the group consisting of: ZEN, IBFQ, BHQ-1, BHQ-2, DDQ-I, DDQ-II, Dabcyl, Qxl quencher, Iowa Black RQ, and IRDye QC-1.

3. The method of claim 1, wherein the sample comprising one or more dNTPs comprises an intracellular sample of dNTPs.

4. The method of claim 3, wherein the intracellular sample is derived from one or more cancer cells.

5. The method of claim 3, wherein the intracellular sample is derived from one or more cells that have been exposed to one or more chemotherapeutic agents.

6. The method of claim 1, wherein the polymerase comprises Taq polymerase.

7. The method of claim 1, wherein the fluorophore is selected from the group consisting of: 6-FAM, TET, HEX, Cy3, TMR, ROX, Texas Red, Cy5, LC red 705 and LC red 640.

8. The method of claim 1, wherein the oligonucleotide template comprises one or more quenchers.

9. The method of claim 8, wherein one or more of the quenchers is a non-fluorescent quencher selected from the group consisting of BHQ-1 and BHQ-2.

10. The method of claim 8, wherein one or more of the quenchers is located on a region of the oligonucleotide template within 1-5 bases of the base opposite where a 5' end of the fluorophore-labeled probe would hybridize under hybridizing conditions.

11. A kit for detecting deoxyribonucleoside triphosphates (dNTPs), comprising: an oligonucleotide template specific for a particular dNTP, wherein the oligonucleotide template comprises a 3' primer binding region adjacent to a dNTP detection region and a 5' fluorophore-labeled probe binding region adjacent to the dNTP detection region; and a fluorophore-labeled probe, wherein (1) the fluorophore-labeled probe is complementary to the 5' fluorophore-labeled probe binding region of the oligonucleotide template, (2) the fluorophore-labeled probe comprises a fluorophore and one or more quenching molecules, configured such that the one or more quenching molecules quench a fluorescence of the fluorophore in the absence of the particular dNTP, and (3) the fluorophore-labeled probe and the oligonucleotide template are configured to allow for the detection of the particular dNTP according to the method of claim 1, when combined with (a) a sample comprising the particular dNTP, (b) a polymerase capable of mediating 5'-3' exonuclease hydrolysis, and (c) a primer complimentary to the 3' primer binding region.

12. The kit of claim 11, wherein one or more of the quenching molecules is a non-emissive (dark) quenching molecule selected from the group consisting of: ZEN, IBFQ, BHQ-1, BHQ-2, DDQ-I, DDQ-II, Dabcyl, Qxl quencher, Iowa Black RQ, and IRDye QC-1.

13. The kit of claim 11, further comprising a primer.

14. The kit of claim 11, further comprising a quantity of dNTPs.

15. The kit of claim 11, further comprising a polymerase capable of mediating 5'-3' exonuclease hydrolysis.

16. The kit of claim 15, wherein the polymerase is Taq polymerase.

17. The kit of claim 11, further comprising instructions for detecting one or more dNTPs.

18. The kit of claim 11, wherein the fluorophore is selected from the group consisting of: 6-FAM, TET, HEX, Cy3, TMR, ROX, Texas Red, Cy5, LC red 705 and LC red 640.

19. The kit of claim 11, wherein the oligonucleotide template comprises one or more quenchers.

20. The kit of claim 19, wherein one or more of the quenchers is a non-fluorescent quencher selected from the group consisting of BHQ-1-dT and BHQ-2.

21. The kit of claim 19, wherein one or more of the quenchers are located on a region of the oligonucleotide template within 1-5 bases of the base opposite where a 5' end of the fluorophore-labeled probe would hybridize under hybridizing conditions.

22. A composition, comprising: an oligonucleotide template specific for a particular dNTP, wherein the oligonucleotide template comprises a 3' primer binding region adjacent to a dNTP detection region and a 5' fluorophore-labeled probe binding region adjacent to the dNTP detection region; a fluorophore-labeled probe bound to said oligonucleotide template, wherein the fluorophore-labeled probe comprises a fluorophore and one or more quenching molecules, and wherein the one or more quenching molecules quenches a fluorescence from the fluorophore in the absence of the particular dNTP; a primer bound to said oligonucleotide template; and a polymerase capable of mediating 5'-3' exonuclease hydrolysis.

23. The composition of claim 22, wherein one or more of the quenching molecules is a non-emissive (dark) quenching molecule selected from the group consisting of: ZEN, IBFQ, BHQ-1, BHQ-2, DDQ-I, DDQ-II, Dabcyl, Qxl quencher, Iowa Black RQ, and IRDye QC-1.

24. The composition of claim 22, wherein the oligonucleotide template further comprises one or more quenchers.

25. The composition of claim 24, wherein one or more of the quenchers are located on a region of the oligonucleotide template within 1-5 bases of the base opposite where a 5' end of the fluorophore-labeled probe would hybridize under hybridizing conditions.

* * * * *